US012097300B2

(12) United States Patent
Chan et al.

(10) Patent No.: US 12,097,300 B2
(45) Date of Patent: Sep. 24, 2024

(54) BIOFUNCTIONAL HYDROGEL FOR WOUND HEALING

(71) Applicant: Nanyang Technological University, Singapore (SG)

(72) Inventors: Bee Eng Mary Chan, Singapore (SG); Chun Kiat Yeo, Singapore (SG); Nguan Soon Tan, Singapore (SG); Surendra Hittanahalli Mahadevegowda, Singapore (SG)

(73) Assignee: Nanyang Technological University, Singapore (SG)

( * ) Notice: Subject to any disclaimer, the term of this patent is extended or adjusted under 35 U.S.C. 154(b) by 602 days.

(21) Appl. No.: 17/167,568

(22) Filed: Feb. 4, 2021

(65) Prior Publication Data
US 2021/0244846 A1 Aug. 12, 2021

(30) Foreign Application Priority Data

Feb. 7, 2020 (SG) .............................. 10202001128R

(51) Int. Cl.
A61L 26/00 (2006.01)
B82Y 5/00 (2011.01)
C08L 79/04 (2006.01)
C08L 81/02 (2006.01)

(52) U.S. Cl.
CPC ......... *A61L 26/008* (2013.01); *A61L 26/0052* (2013.01); *A61L 26/0066* (2013.01); *C08L 79/04* (2013.01); *C08L 81/02* (2013.01); *A61L 2400/12* (2013.01); *B82Y 5/00* (2013.01)

(58) Field of Classification Search
CPC ............... A61L 26/008; A61L 26/0052; A61L 26/0066; A61L 2400/12; B82Y 5/00
See application file for complete search history.

(56) References Cited

U.S. PATENT DOCUMENTS 9,131,692 B2 9/2015 Kim et al.
2013/0287742 A1* 10/2013 Kaplan .................. A61L 27/26
106/156.1

FOREIGN PATENT DOCUMENTS

WO WO-2016168196 A1 * 10/2016 ............. A61L 27/18

OTHER PUBLICATIONS

Luo et al. "In Situ covalently cross-linked PEG hydrogel for ocular drug delivery applications," in International Journal of Pharmaceutics, 470 (2014) 151-157. (Year: 2014).*
Phelps et al., "Maleimide Cross-Linked Bioactive PEG hydrogel Exhibits Improved Reaction Kinetics and cross-Linking for Cell Encapsulation and In Situ Delivery" in Advanced Materials, 2012, 64-70 (Year: 2012).*
Lindner; Imidazolium-Based Polymers via the Poly-Radziszewski Reaction; Macromolecules 2016, 49, 2046-2053.
Nair et al.; The Thiol-Michael Addition Click Reaction: A Powerful and Widely; Used Tool in Materials Chemistry; Chem. Mater. 2013, 26, 724-744.

(Continued)

*Primary Examiner* — Blessing M Fubara
(74) *Attorney, Agent, or Firm* — Patterson + Sheridan, LLP

(57) ABSTRACT

Disclosed herein is a hydrogel that eradicates biofilm bacteria from wounds and accelerates diabetic wound healing. Also disclosed herein are methods of manufacture and use of said hydrogel.

19 Claims, 14 Drawing Sheets

(56) References Cited

OTHER PUBLICATIONS

Martínez-Jothar et al.; Insights into maleimide-thiol conjugation chemistry: Conditions for efficient surface functionalization of nanoparticles for receptor targeting; J. Control. Release 2018, 282, 101-109.

Kirkup Jr; Bacterial Strain Diversity Within Wounds; Adv Wound Care (New Rochelle) 2015, 4, 12-23.

Dunnill et al.; Reactive oxygen species (ROS) and wound healing: the functional role of ROS and emerging ROS-modulating technologies for augmentation of the healing process; Int. Wound J. 2017, 14, 89-96.

Curatolo et al.; Transient instabilities in the swelling dynamics of a hydrogel sphere; J. Appl. Phys. 2017, 122, 145109.

Alegre-Requena et al.; Understanding hydrogelation processes through molecular dynamics; J. Mater. Chem. B. 2019, 7, 1652-1673.

Chen, S. et al.; Dissipative particle dynamics modeling of hydrogel swelling by osmotic ensemble method; J. Chem. Phys. 2018, 149, 094904.

Tan et al.; StudyingWound Repair in the Mouse; Curr Protoc Mouse Biol 2013, 3, 171-185.

Hariono. et al.; StudyingWound Repair in the Mouse; Wound Medicine 2018, 22, 1-13.

Han et al.; Chronic Wound Healing: A Review of Current; Management and Treatments; Adv Ther 2017, 34 (3), 599-610.

Simoes, D. et al.; Recent advances on antimicrobial wound dressing: A review; Eur J Pharm Biopharm 2018, 127, 130-141.

Stamatas et al.; Early Inflammatory Processes in the Skin; Current Molecular Medicine 2013, 13 (8), 1250-1269.

Almahmoud et al.; Computational evidence for an early,; amplified systemic inflammation program in; polytrauma patients with severe extremity; injuries; PLoS One 2019, 14 (6), e0217577.

Eming et al.; Interrelation of immunity and tissue repair or regeneration; Semin Cell Dev Biol 2009, 20 (5), 517-27.

Eming et al.; Differential Proteomic Analysis Distinguishes Tissue Repair Biomarker Signatures in Wound Exudates Obtained from Normal Healing and Chronic Wounds; Journal of Proteome Research 2010, 9 (9), 4758-4766.

Beidler et al.,; Inflammatory cytokine levels in chronic venous insufficiency ulcer tissue before and after compression therapy; J Vasc Surg 2009, 49 (4), 1013-20.

Edwards, et al.; Bacteria and wound healing; Current Opinion in Infectious Diseases 2004, 17, 91-96.

Koh et al.; Inflammation and wound healing: the role of the macrophage L. A. Expert Rev Mol Med 2011, 13, e23.

Koumakis et al.; Novel function of PiT1/SLC20A1in LPS-related inflammation and wound healing; Sci Rep 2019, 9 (1), 1808.

Pastar et al.; Interactions of Methicillin Resistant *Staphylococcus aureus* USA300 and *Pseudomonas aeruginosa* in Polymicrobial Wound Infection; PLoS One 2013, 8 (2), e56846.

Trøstrup et al.; Chronic Pseudomonas aeruginosa biofilm infection impairs murine S100A8/A9 and neutrophil effector cytokines-implications for delayed wound closure?; Pathog Dis 2017, 75 (7), ftx110.

Gardner et al.; Wound Bioburden and Infection-Related Complications in Diabetic Foot Ulcers; Biological Research for Nursing 2008, 10 (1), 44-53.

Sjogren et al.; Negative-pressure wound therapy following cardiac surgery: bleeding complications and 30-day mortality in 176 patients with deep sternal wound infection; Interact Cardiovasc Thorac Surg 2011, 12 (2), 117-20.

Fife et al.; Wound Care Outcomes and; Associated Cost Among Patients; Treated in US Outpatient Wound; Centers: Data From the US Wound; Registry; Wounds 2012, 24 (1), 10-17.

Bhattacharya et al.; Effect of Bacteria on the Wound Healing Behavior of Oral Epithelial Cells; PLoS One 2014, 9 (2), e89475.

Agyingi et al.; The Effect of Bacteria on Epidermal Wound Healing; Mathematical Modelling of Natural Phenomena 2010, 5 (3), 28-39.

Guzik et al.; Mechanisms of Increased Vascular Superoxide Production in Human Diabetes Mellitus; Circulation 2002, 105 (14), 1656-1662.

Chen et al.; Dynamic covalent constructed self-healing hydrogel for sequential delivery of antibacterial agent and growth factor in wound healing; Chemical Engineering Journal 2019, 373, 413-424.

Muhamed et al.; Fibrin Nanoparticles Coupled with Keratinocyte Growth Factor Enhance the Dermal Wound-Healing Rate; ACS Appl Mater Interfaces 2019, 11 (4), 3771-3780.

Aragona et al.; Defining stem cell dynamics and migration during wound healing in mouse skin epidermis; Nat Commun 2017, 8, 14684.

Lee et al.; Mesenchymal stem cells and cutaneous wound healing: novel methods to increase cell delivery and therapeutic efficacy; Stem Cell Res Ther 2016, 7, 37.

Dash et al.; Targeting Nonhealing Ulcers of Lower Extremity in Human Through Autologous Bone Marrow-Derived Mesenchymal Stem Cells; Rejuvenation Research 2009, 12 (5), 359-366.

Castleberryet al.; Self-Assembled Wound Dressings Silence MMP-9 and Improve Diabetic Wound Healing In Vivo; Adv Mater 2016, 28 (9), 1809-17.

Samuni et al.; The chemistry and biological activities of N-acetylcysteine; Biochim Biophys Acta 2013, 1830 (8), 4117-29.

Aldini et al.; N-Acetylcysteine as an antioxidant and disulphide breaking agent: the reasons why; Free Radic Res 2018, 52 (7), 751-762.

Atkuri et al.; N-Acetylcysteine-a safe antidote for cysteine/glutathione Deficiency; Curr Opin Pharmacol 2007, 7 (4), 355-9.

Kopke et al.; NAC for noise: From the bench top to the clinic; Hear Res 2007, 226 (1-2), 114-25.

Aktunc et al.; N-acetyl cysteine promotes angiogenesis and clearance of free oxygen radicals, thus improving wound healing in an alloxan-induced diabetic mouse model of incisional wound; Clin Exp Dermatol 2010, 35 (8), 902-9.

Oguz et al.; Topical N-Acetylcysteine Improves Wound Healing Comparable to Dexpanthenol: An Experimental Study; Int Surg 2015, 100 (4), 656-61.

Tsai et al.; Topical N-Acetylcysteine Accelerates Wound Healing in Vitro and in Vivo via the PKC/Stat3 Pathway; Int J Mol Sci 2014, 15 (5), 7563-78.

Yeo et al., Hydrogel Effects Rapid Biofilm Debridement with ex situ Contact-Kill to Eliminate Multidrug Resistant Bacteria in vivo; ACS Appl Mater Interfaces 2018, 10 (24), 20356-20367.

Noor et al.; Diabetic foot ulcer—A review on pathophysiology, classification and microbial etiology; Diabetes Metab Syndr 2015, 9 (3), 192-9.

Forman et al.; Glutathione: Overview of its protective roles, measurement, and biosynthesis; Mol Aspects Med 2009, 30 (1-2), 1-12.

Jault et al.; Efficacy and tolerability of a cocktail of bacteriophages to treat burn wounds infected by *Pseudomonas aeruginosa* (PhagoBurn): a randomised, controlled, double-blind phase 1/2 trial; The Lancet Infectious Diseases 2019, 19 (1), 35-45.

Manzuoerh et al.; Effectiveness of topical administration of Anethum graveolens essential oil on MRSA-infected wounds; Biomed Pharmacother 2019, 109, 1650-1658.

Chen et al.; Exosomal DMBT1 from human urine-derived stem cells facilitates diabetic wound repair by promoting angiogenesis; Theranostics 2018, 8 (6), 1607-1623.

Guo et al.; Exosomes derived from platelet-rich plasma promote the re-epithelization of chronic cutaneous wounds via activation of YAP in a diabetic rat model; Theranostics 2017, 7 (1), 81-96.

Tan et al.; Studying Wound Repair in the Mouse; Protoc Mouse Biol 2013, 3 (3), 171-85.

Navath et al.; Stimuli-responsive star polyethylene glycol conjugates for improved intracellular delivery of N-acetyl cysteine in neuro inflammation; J Control Release 2010, 142, 447-456.

World Health Organization; WHO publishes list of bacteria for which new antibiotics are urgently needed; (Feb. 27, 2017).

Jewett et al.; Rapid Cu-Free Click Chemistry with Readily Synthesized Biarylazacyclooctynones; J. Am. Chem. Soc. 2010, 132, 3688-3690.

(56) References Cited

OTHER PUBLICATIONS

Stewart et al.; Synthetic hydrogels formed by thiol-ene; crosslinking of vinyl sulfone-functional poly (methyl vinyl ether-alt-maleic acid); with a,x-dithio-polyethyleneglycol; Soft Matter, 2018, 14, 8317-8324.

* cited by examiner

BIOFUNCTIONAL HYDROGEL FOR WOUND HEALING

FIELD OF INVENTION

This invention relates to the field of hydrogels, particularly hydrogels that can be used in wound healing applications. The invention also relates to the manufacture and use of the hydrogels.

BACKGROUND

The listing or discussion of a prior-published document in this specification should not necessarily be taken as an acknowledgement that the document is part of the state of the art or is common general knowledge.

Wound healing consists of three main stages: inflammation, proliferation, and maturation. However, inflammation is prolonged in chronic wounds and wound healing might fail to progress to later stages. Recent research on chronic wound tissue and fluid revealed a continual competition between inflammatory and anti-inflammatory signals that leads to an imbalanced environment for proper wound healing to occur.

Bacterial colonization of wounds is common and could lead to wound infection, which is likely to be a contributing factor for prolonged inflammation and delayed wound healing. As all wounds are colonized by bacteria to some degree, a major role of the inflammatory phase of wound healing is to bring microbes down to steady-state and innocuous levels. However, in these polymicrobial wound communities, the microbes may become more virulent and proliferate to form a biofilm that further impedes wound healing. Besides delaying wound healing, wound infections can lead to serious complications such as amputations and death. Therefore, the elimination of bacterial infection is a crucial step in wound healing because bacteria typically disrupt the natural healing process and deteriorates the wound.

Chronic non-healing infected wounds in patients with diabetes are a significant medical problem with potentially serious consequences. However, multi-drug resistance and the refractory character of bacterial biofilms, which are common in such wounds, complicate treatment. Current FDA-approved treatments for diabetic wounds are limited by their contraindications, and antimicrobial strategies for treating wounds, such as silver dressings, are typically prophylactic rather than curative. In addition, current wound dressings focus only on one aspect of wound healing or on one type of wound (chronic or diabetic).

Therefore, there is a need to seek new strategies to address the underlying problems of wound repair such as infection, increased oxidative stress and inflammation, and reduced angiogenesis and fibroblast migration/proliferation, to accelerate chronic or diabetic wound healing.

SUMMARY OF INVENTION

Aspects and embodiments of the current invention will be described by reference to the following numbered clauses.

1. A hydrogel for wound healing comprising:
   a hydrogel polymeric matrix comprising:
      a first polymeric component;
      a second polymeric component, where the first and second polymeric components are crosslinked together to form the hydrogel polymeric matrix; and
      a first portion of a polymeric antimicrobial material capable of crosslinking with the first and/or second polymeric components, said material being wholly or partly crosslinked into the hydrogel polymeric matrix;
   a second portion of the polymeric antimicrobial material capable of crosslinking with the first and/or second polymeric components distributed within the hydrogel polymeric matrix; and
   optionally, an antioxidant material distributed within the hydrogel polymeric matrix and/or covalently bonded thereto.

2. The hydrogel according to Clause 1, wherein the first and second polymeric components are selected from one of the following sets:
   (a) the first polymeric component is derived from a polymeric material comprising at least two thiol functional groups and the second polymeric component is derived from a polymeric material comprising at least two maleimide groups;
   (b) the first polymeric component is derived from a polymeric material comprising at least two thiol functional groups and the second polymeric component is derived from a polymeric material comprising at least two vinyl sulfone groups;
   (c) the first polymeric component is derived from a polymeric material comprising at least two azide functional groups and the second polymeric component is derived from a polymeric material comprising at least two cyclooctynyl groups;
   (d) the first polymeric component is derived from a polymeric material comprising at least two amine functional groups and the second polymeric component is derived from a polymeric material comprising at least two aldehyde groups; and
   (e) the first polymeric component is derived from a polymeric material comprising at least two amine functional groups and the second polymeric component is derived from a polymeric material comprising at least two acrylate groups.

3. The hydrogel according to Clause 2, wherein the first polymeric component is derived from a polymeric material comprising at least two thiol functional groups and the second polymeric component is derived from a polymeric material comprising at least two maleimide groups.

4. The hydrogel according to Clause 3, wherein the first polymeric component is derived from a polymeric material that has from 2 to 8 thiol functional groups and the second polymeric component is derived from a polymeric material that has from 2 to 8 maleimide groups.

5. The hydrogel according to Clause 4, wherein the first polymeric component is derived from a multi-arm polyethylene glycol having from 2 to 8 arms that are each terminated by a thiol functional group and the second polymeric component is derived from a multi-arm polyethylene glycol having from 2 to 8 arms that are each terminated by a maleimide group.

6. The hydrogel according to Clause 5, wherein the first polymeric component is derived from poly(ethylene glycol) tetra thiol and the second polymeric component is derived from poly(ethylene glycol) tetra maleimide.

7. The hydrogel according to any one of the preceding clauses, wherein the polymeric antimicrobial material capable of crosslinking with the first and/or second polymeric components is selected from one or more of a polycationic polymer terminated by at least two maleimide groups, a polycationic polymer terminated by at least one maleimide group and at least one thiol group, a polycationic polymer terminated by at least two vinyl sulfone groups, a polycationic polymer terminated by at least one vinyl sulfone group and at least one thiol group, a polycationic polymer terminated by at least two cyclooctynyl groups, a polycationic polymer terminated by at least two azide groups, a polycationic polymer terminated by at least one cyclooctynyl group and at least one azide group, a polycationic polymer terminated by at least two amino groups, a polycationic polymer terminated by at least two aldehyde groups, a polycationic polymer terminated by at least one amino group and at least one aldehyde group, a polycationic polymer terminated by at least two acrylate groups, and a polycationic polymer terminated by at least one amino group and at least one acrylate group provided that said material is capable of forming a crosslink with at least one of the first and second polymeric components.

8. The hydrogel according to Clause 7, wherein the polymeric antimicrobial material is a polycationic polymer terminated by at least two maleimide groups, optionally wherein the polycationic polymer is terminated by two maleimide groups.

9. The hydrogel according to Clause 8, wherein the polymeric antimicrobial material is a polyimidazolium polymer terminated by two maleimide groups.

10. The hydrogel according to any one of the preceding clauses, wherein the polymeric antimicrobial material capable of crosslinking with the first and/or second polymeric components has a number average molecular weight of from 500 Daltons to 50,000 Daltons.

11. The hydrogel according to Clause 10, wherein the polymeric antimicrobial material has a number average molecular weight of from 1,000 Daltons to 15,000 Daltons.

12. The hydrogel according to Clause 11, wherein the polymeric antimicrobial material has a number average molecular weight of from 2,000 Daltons to 10,000 Daltons, optionally wherein the polymeric antimicrobial material has a number average molecular weight of about 2,766 Daltons.

13. The hydrogel according to any one of the preceding clauses, wherein the antioxidant material is present, optionally wherein the antioxidant material is N-acetyl cysteine.

14. The hydrogel according to any one of the preceding clauses, wherein the hydrogel is in a form selected from a film, nanoparticles and microparticles.

15. A composite material comprising a substrate and a coating formed of a hydrogel as described in any one of Clauses 1 to 14, optionally wherein the substrate is a foam.

16. A kit of parts selected from:

(i)
  (ia) a first mixture comprising a first polymer capable of crosslinking with a second polymer and, optionally, an antioxidant material as described in any one of Clauses 1 to 14 (e.g. a first mixture comprising a first polymer capable of crosslinking with a second polymer and an antioxidant material as described in any one of Clauses 1 to 14);
  (ib) a second mixture comprising a second polymer and a polymeric antimicrobial material capable of crosslinking with the first polymer; and
  (ic) a pharmaceutically acceptable solvent;
  or
(ii) (iia) a first mixture comprising a first polymer capable of crosslinking with a second polymer, and a polymeric antimicrobial material capable of crosslinking with the second polymer and, optionally, an antioxidant material as described in any one of Clauses 1 to 14 (e.g. a first mixture comprising a first polymer capable of crosslinking with a second polymer, a polymeric antimicrobial material capable of crosslinking with the second polymer, and an antioxidant material as described in any one of Clauses 1 to 14);
  (iib) a second mixture comprising a second polymer; and
  (iic) a pharmaceutically acceptable solvent;
  or
(iii) (iiia) a first mixture comprising a first polymer capable of crosslinking with a second polymer and a polymeric antimicrobial material capable of crosslinking with the second polymer;
  (iiib) a second mixture comprising a second polymer and, optionally, an antioxidant material as described in any one of Clauses 1 to 14 (e.g. a second mixture comprising a second polymer capable of crosslinking with the first polymer and an antioxidant material as described in any one of Clauses 1 to 14); and
  (iiic) a pharmaceutically acceptable solvent;
  or
(iv) (iva) a first mixture comprising a first polymer capable of crosslinking with a second polymer and, optionally, an antioxidant material as described in any one of Clauses 1 to 14 (e.g. a first mixture comprising a first polymer capable of crosslinking with a second polymer and an antioxidant material as described in any one of Clauses 1 to 14);
  (ivb) a second mixture comprising a second polymer;
  (ivc) a pharmaceutically acceptable solvent; and
  (ivd) a polymeric antimicrobial material capable of crosslinking with the first and second polymers.

17. A method of forming a hydrogel according to any one of Clauses 1 to 14, comprising the steps of:
(AA) providing at least two separate solutions, each of said solutions containing a solvent, where each of the at least two solutions contain one or more of a first polymer capable of crosslinking with a second polymer, a second polymer capable of crosslinking with the first polymer, a polymeric antimicrobial material capable of crosslinking with the first and/or second polymer, and, optionally, an antioxidant material as described in any one of Clauses 1 to 14, provided that materials that can react together are not contained in the same solution; and
(BB) mixing the at least two solutions together to form the hydrogel according to any one of Clauses 1 to 14.

18. The kit of parts according to Clause 16 or the method according to Clause 17, wherein one or more of the following apply:
(A) the first and second polymers are selected from one of the following sets:
  (aa) the first polymer is a polymeric material comprising at least two thiol functional groups and the second polymer is a polymeric material comprising at least two maleimide groups;

(bb) the first polymer is a polymeric material comprising at least two thiol functional groups and the second polymer is a polymeric material comprising at least two vinyl sulfone groups;
(cc) the first polymer is a polymeric material comprising at least two azide functional groups and the second polymer is a polymeric material comprising at least two cyclooctynyl groups;
(dd) the first polymer is a polymeric material comprising at least two amine functional groups and the second polymer is a polymeric material comprising at least two aldehyde groups; and
(ee) the first polymer is a polymeric material comprising at least two amine functional groups and the second polymer is a polymeric material comprising at least two acrylate groups;

(B) the first polymer is a polymeric material comprising at least two thiol functional groups and the second polymer is a polymeric material comprising at least two maleimide groups, optionally wherein:
(ff) the first polymer is a polymeric material that has from 2 to 8 thiol functional groups and the second polymer is a polymeric material that has from 2 to 8 maleimide groups;
(gg) the first polymer is a multi-arm polyethylene glycol having from 2 to 8 arms that are each terminated by a thiol functional group and the second polymer is a multi-arm polyethylene glycol having from 2 to 8 arms that are each terminated by a maleimide group;
(hh) the first polymer is poly(ethylene glycol) tetra thiol and the second polymer is poly(ethylene glycol) tetra maleimide;

(C) the polymeric antimicrobial material capable of crosslinking with the first and/or second polymers is selected from one or more of a polycationic polymer terminated by at least two maleimide groups, a polycationic polymer terminated by at least one maleimide group and at least one thiol group, a polycationic polymer terminated by at least two vinyl sulfone groups, a polycationic polymer terminated by at least one vinyl sulfone group and at least one thiol group, a polycationic polymer terminated by at least two cyclooctynyl groups, a polycationic polymer terminated by at least two azide groups, a polycationic polymer terminated by at least one cyclooctynyl group and at least one azide group, a polycationic polymer terminated by at least two amino groups, a polycationic polymer terminated by at least two aldehyde groups, a polycationic polymer terminated by at least one amino group and at least one aldehyde group, a polycationic polymer terminated by at least two acrylate groups, and a polycationic polymer terminated by at least one amino group and at least one acrylate group provided that said material is capable of forming a crosslink with at least one of the first and second polymers, optionally wherein:
(ii) the polymeric antimicrobial material is a polycationic polymer terminated by at least two maleimide groups, optionally wherein the polycationic polymer is terminated by two maleimide groups;
(jj) the polymeric antimicrobial material is a polyimidazolium polymer terminated by two maleimide groups;

(D) the polymeric antimicrobial material capable of crosslinking with the first and/or second polymers has a number average molecular weight of from 500 Daltons to 50,000 Daltons, optionally wherein:
(kk) the polymeric antimicrobial material has a number average molecular weight of from 500 Daltons to 50,000 Daltons;
(ll) the polymeric antimicrobial material has a number average molecular weight of from 1,000 Daltons to 15,000 Daltons;
(mm) the polymeric antimicrobial material has a number average molecular weight of from 2,000 Daltons to 10,000 Daltons;
(nn) the polymeric antimicrobial material has a number average molecular weight of about 2,766 Daltons.

19. Use of a hydrogel according to any one of Clauses 1 to 14 in the manufacture of a medicament for wound healing.

20. A method of wound healing comprising applying a hydrogel according to any one of Clauses 1 to 14 to a subject in need thereof.

21. The method according to Clause 20, wherein the hydrogel is formed in situ at a wound site on the subject.

DESCRIPTION

Figure 1:
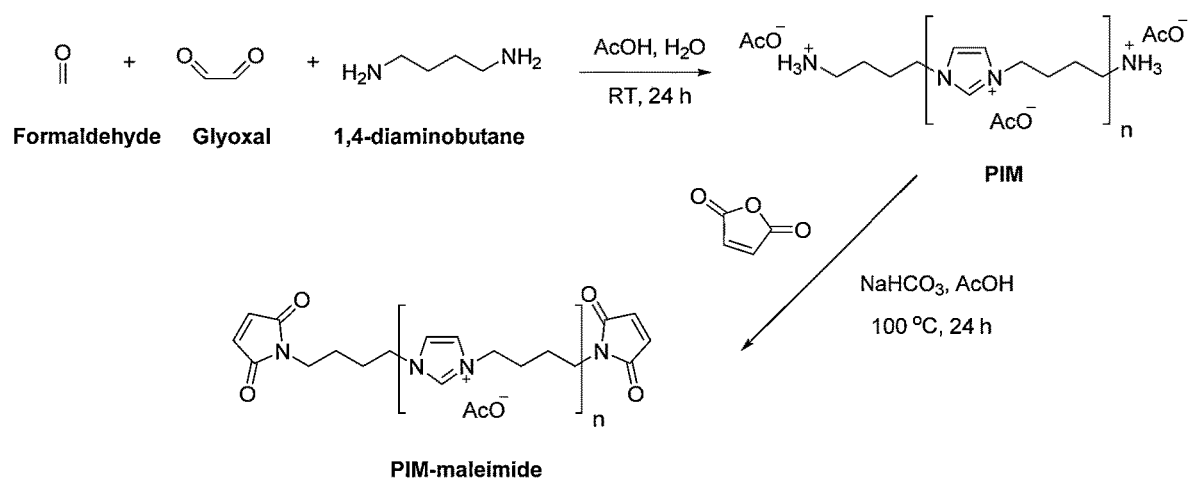
FIG. 1 illustrates the reaction scheme of synthesis of maleimide-terminated polyimidazolium (PIM-mal).

It has been surprisingly found that a hydrogel suitable for use in wound healing can be created by forming a hydrogel that contains at least a polymeric antimicrobial material and an antioxidant material where at least part of these materials are covalently bound to a hydrogel polymeric material.

Thus, in a first aspect of the invention, there is provided a hydrogel for wound healing comprising:
a hydrogel polymeric matrix comprising:
 a first polymeric component;
 a second polymeric component, where the first and second polymeric components are crosslinked together to form the hydrogel polymeric matrix; and
 a first portion of a polymeric antimicrobial material capable of crosslinking with the first and/or second polymeric components, said material being wholly or partly crosslinked into the hydrogel polymeric matrix;
a second portion of the polymeric antimicrobial material capable of crosslinking with the first and/or second polymeric components distributed within the hydrogel polymeric matrix; and
optionally, an antioxidant material distributed within the hydrogel polymeric matrix and/or covalently bonded thereto.

For the avoidance of doubt, this aspect contains two specific generic embodiments. The first is one in which there is provided a hydrogel for wound healing comprising:
a hydrogel polymeric matrix comprising:
 a first polymeric component;
 a second polymeric component, where the first and second polymeric components are crosslinked together to form the hydrogel polymeric matrix; and
 a first portion of a polymeric antimicrobial material capable of crosslinking with the first and/or second polymeric components, said material being wholly or partly crosslinked into the hydrogel polymeric matrix;
an antioxidant material distributed within the hydrogel polymeric matrix and/or covalently bonded thereto; and
a second portion of the polymeric antimicrobial material capable of crosslinking with the first and/or second polymeric components distributed within the hydrogel polymeric matrix. That is, an embodiment where an antioxidant is present. This may be a particularly preferred embodiment.

The second is one in which there is provided a hydrogel for wound healing comprising:
a hydrogel polymeric matrix comprising:
 a first polymeric component;
 a second polymeric component, where the first and second polymeric components are crosslinked together to form the hydrogel polymeric matrix; and
 a first portion of a polymeric antimicrobial material capable of crosslinking with the first and/or second polymeric components, said material being wholly or partly crosslinked into the hydrogel polymeric matrix; and
a second portion of the polymeric antimicrobial material capable of crosslinking with the first and/or second polymeric components distributed within the hydrogel polymeric matrix. That is, the antioxidant material is not present.

In embodiments herein, the word "comprising" may be interpreted as requiring the features mentioned, but not limiting the presence of other features. Alternatively, the word "comprising" may also relate to the situation where only the components/features listed are intended to be present (e.g. the word "comprising" may be replaced by the phrases "consists of" or "consists essentially of"). It is explicitly contemplated that both the broader and narrower interpretations can be applied to all aspects and embodiments of the present invention. In other words, the word "comprising" and synonyms thereof may be replaced by the phrase "consisting of" or the phrase "consists essentially of" or synonyms thereof and vice versa.

The phrase, "consists essentially of" and its pseudonyms may be interpreted herein to refer to a material where minor impurities may be present. For example, the material may be greater than or equal to 90% pure, such as greater than 95% pure, such as greater than 97% pure, such as greater than 99% pure, such as greater than 99.9% pure, such as greater than 99.99% pure, such as greater than 99.999% pure, such as 100% pure.

The term "hydrogel" when used herein takes its ordinary meaning in the art, but may particularly refer to hydrogels where crosslinking between the first and second polymeric components is by covalent bonding. Thus, a "hydrogel polymeric matrix" refers to the base polymer matrix formed by the first and the second polymeric components that are crosslinked together (e.g. by covalent bonding).

The first and second polymeric components may be any suitable polymeric materials that are capable of forming a hydrogel when subjected to suitable conditions. For example, the first and second polymeric components may be selected from one of the following sets:
(a) the first polymeric component may be derived from a polymeric material comprising at least two thiol functional groups and the second polymeric component may be derived from a polymeric material comprising at least two maleimide groups;
(b) the first polymeric component may be derived from a polymeric material comprising at least two thiol functional groups and the second polymeric component may be derived from a polymeric material comprising at least two vinyl sulfone groups;

(c) the first polymeric component may be derived from a polymeric material comprising at least two azide functional groups and the second polymeric component may be derived from a polymeric material comprising at least two cyclooctynyl groups;

(d) the first polymeric component may be derived from a polymeric material comprising at least two amine functional groups and the second polymeric component may be derived from a polymeric material comprising at least two aldehyde groups; and (e) the first polymeric component may be derived from a polymeric material comprising at least two amine functional groups and the second polymeric component may be derived from a polymeric material comprising at least two acrylate groups.

As will be appreciated, the materials above may form a hydrogel by the formation of covalent bonds between the first and the second polymeric components. It is also noted that each of the first and the second polymeric components listed above require at least two functional groups that are capable of forming crosslinks with the other component. However, the total number of functional groups that can form said covalent bonds may significantly exceed this limitation. For example, the first and/or the second polymeric component may each independently have from 2 to 20, such as from 2 to 10, such as from 4 to 8 functional groups capable of forming a covalent bond with the other component. In particular embodiments of the invention that may be mentioned herein, the first and/or second polymeric component may have 4 functional groups capable of forming a covalent bond with the other component.

In an embodiment of the invention that may be mentioned herein, the first polymeric component may be derived from a polymeric material comprising at least two thiol functional groups and the second polymeric component may be derived from a polymeric material comprising at least two maleimide groups. For example, the first polymeric component may be derived from a polymeric material that has from 2 to 8 thiol functional groups and the second polymeric component may be derived from a polymeric material that has from 2 to 8 maleimide groups. More particularly, the first polymeric component may be derived from a multi-arm polyethylene glycol having from 2 to 8 arms that are each terminated by a thiol functional group and the second polymeric component may be derived from a multi-arm polyethylene glycol having from 2 to 8 arms that are each terminated by a maleimide group. Yet more particularly, the first polymeric component may be derived from poly(ethylene glycol) tetra thiol and the second polymeric component may be derived from poly(ethylene glycol) tetra maleimide.

The number average molecular weight of the first and second polymeric components may independently be from 10,000 to 50,000 Daltons, such as from 15,000 to 25,000 Daltons, such as about 20,000 Daltons.

In order to provide the desired functionality, the hydrogel described herein also contains a at least a polymeric antimicrobial material.

The polymeric antimicrobial material may be any suitable material, provided that it is capable of forming crosslinks with at least one of the first and second polymeric components. For example, the polymeric antimicrobial material capable of crosslinking with the first and/or second polymeric components may be selected from one or more of a polycationic polymer terminated by at least two maleimide groups, a polycationic polymer terminated by at least one maleimide group and at least one thiol group, a polycationic polymer terminated by at least two vinyl sulfone groups, a polycationic polymer terminated by at least one vinyl sulfone group and at least one thiol group, a polycationic polymer terminated by at least two cyclooctynyl groups, a polycationic polymer terminated by at least two azide groups, a polycationic polymer terminated by at least one cyclooctynyl group and at least one azide group, a polycationic polymer terminated by at least two amino groups, a polycationic polymer terminated by at least two aldehyde groups, a polycationic polymer terminated by at least one amino group and at least one aldehyde group, a polycationic polymer terminated by at least two acrylate groups, and a polycationic polymer terminated by at least one amino group and at least one acrylate group provided that said material is capable of forming a crosslink with at least one of the first and second polymeric components.

Yet more particularly, based on the materials disclosed above for the first and second polymeric components, the following combinations may be contemplated:

when the first polymeric component is derived from a polymeric material comprising at least two thiol functional groups and the second polymeric component is derived from a polymeric material comprising at least two maleimide groups, then the polymeric antimicrobial material may be a polycationic polymer terminated by at least two maleimide groups or a polycationic polymer terminated by at least one maleimide group and at least one thiol group, when the first polymeric component is derived from a polymeric material comprising at least two thiol functional groups and the second polymeric component is derived from a polymeric material comprising at least two vinyl sulfone groups, then the polymeric antimicrobial material may be a polycationic polymer terminated by at least two maleimide groups, a polycationic polymer terminated by at least two vinyl sulfone groups, or a polycationic polymer terminated by at least one vinyl sulfone group and at least one thiol group;

when the first polymeric component is derived from a polymeric material comprising at least two azide functional groups and the second polymeric component is derived from a polymeric material comprising at least two cyclooctynyl groups, then the polymeric antimicrobial material may be a polycationic polymer terminated by at least two cyclooctynyl groups, a polycationic polymer terminated by at least two azide groups, or a polycationic polymer terminated by at least one cyclooctynyl group and at least one azide group;

when the first polymeric component is derived from a polymeric material comprising at least two amine functional groups and the second polymeric component is derived from a polymeric material comprising at least two aldehyde groups, then the polymeric antimicrobial material may be a polycationic polymer terminated by at least two amino groups, a polycationic polymer terminated by at least two aldehyde groups, or a polycationic polymer terminated by at least one amino group and at least one aldehyde group; and when the first polymeric component is derived from a polymeric material comprising at least two amine functional groups and the second polymeric component is derived from a polymeric material comprising at least two acrylate groups, then the polymeric antimicrobial material may be a polycationic polymer terminated by at least two acrylate groups, or a polycationic polymer terminated by at least one amino group and at least one acrylate group.

As will be appreciated, in the combinations listed above, the polymeric antimicrobial materials are capable of forming a crosslink with at least one of the first and second polymeric components with which they are combined with. It is also noted that each of the polymeric antimicrobial materials listed above require at least two functional groups that are capable of forming crosslinks with the first and/or second polymeric components. However, the total number of functional groups that can form said covalent bonds may significantly exceed this limitation. For example, the polymeric antimicrobial material may have from 2 to 20, such as from 2 to 10, such as from 4 to 8 functional groups capable of forming a covalent bond with the first and/or second polymeric components. In particular embodiments of the invention that may be mentioned herein, the polymeric antimicrobial material may have 2 functional groups capable of forming a covalent bond with the first and/or second polymeric components.

In particular embodiments that may be mentioned herein, the polymeric antimicrobial material capable of crosslinking with the first and/or second polymeric components may be selected from one or more of a polycationic polymer terminated by two maleimide groups, a polycationic polymer terminated by a maleimide group and a thiol group, a polycationic polymer terminated by two vinyl sulfone groups, a polycationic polymer terminated by a vinyl sulfone group and a thiol group, a polycationic polymer terminated by two cyclooctynyl groups, a polycationic polymer terminated by two azide groups, a polycationic polymer terminated by a cyclooctynyl group and an azide group, a polycationic polymer terminated by two amino groups, a polycationic polymer terminated by two aldehyde groups, a polycationic polymer terminated by an amino group and an aldehyde group, a polycationic polymer terminated by two acrylate groups, and a polycationic polymer terminated by an amino group and an acrylate group, provided that said material is capable of forming a crosslink with at least one of the first and second polymeric components.

While the polymeric antimicrobial material must be capable of forming covalent bonds between itself and at least one of the first and second polymeric components, that does not necessarily mean that all of said material does so. For example, some of the polymeric antimicrobial material may not react at all with the first and/or the second polymeric components and so may simply be distributed within the polymeric matrix. On the other hand, the remaining polymeric antimicrobial material may react wholly or partly with the first and/or the second polymeric components to generate covalent bonds between these components. As such, part of the material may be entirely crosslinked, part of the material may be partly crosslinked (e.g. when there are two functional groups capable of forming a covalent bond with the first and/or the second polymeric components, only one does so; or when there are three functional groups capable of forming a covalent bond with the first and/or the second polymeric components, only two do so), and part of the material may not form any covalent bonds with the first and/or the second polymeric components and may instead be distributed within the polymeric matrix of the hydrogel. In embodiments of the invention that may be mentioned herein, the proportion of the antimicrobial material in each of the three states mentioned above may be randomly distributed.

In particular embodiments of the invention that may be mentioned herein, the polymeric antimicrobial material may be a polycationic polymer terminated by at least two maleimide groups. For example, it may be a polycationic polymer terminated by two maleimide groups. More particularly, the polymeric antimicrobial material may be a polyimidazolium polymer terminated by two maleimide groups. In particular examples that may be mentioned herein, the repeating unit of the polyimidazolium polymer may have from 2 to 7, such as from 3 to 5, such as 4 acyclic carbon atoms in a linear chain (e.g. see the polyimidazolium polymer depicted in FIG. 1). Any suitable anion that is pharmaceutically acceptable may be used as the counterionic species to the cationic polymer. For example, the anion may be the acetate anion.

Any suitable molecular weight for the polymeric antimicrobial material may be used herein. For example, the polymeric antimicrobial material capable of crosslinking with the first and/or second polymeric components may have a number average molecular weight of from 500 Daltons to 50,000 Daltons. More particularly, the polymeric antimicrobial material may have a number average molecular weight of from 1,000 Daltons to 15,000 Daltons. Yet more particularly, the polymeric antimicrobial material may have a number average molecular weight of from 2,000 Daltons to 10,000 Daltons. For example, the polymeric antimicrobial material capable of crosslinking with the first and/or second polymeric components may have a number average molecular weight of about 2,766 Daltons.

In certain embodiments that may provide enhanced functionality (e.g. improved wound healing), the hydrogel described herein may also include an antioxidant material. When referred to herein, the improved wound healing may be measured, for example, by comparison to a material of the current invention as described herein that does not include an antioxidant material.

Any suitable antioxidant material may be used in the hydrogel of the current invention. Examples of suitable antioxidant materials that may be used include, but are not limited to N-acetyl cysteine. In particular embodiments that may be mentioned herein, the antioxidant material may be N-acetyl cysteine.

As noted above, the antioxidant material may be distributed within the hydrogel polymeric matrix or it may be covalently bonded thereto, or a portion may be distributed within the hydrogel polymeric matrix and a portion may be covalently bonded to the first and/or second polymeric components.

In particular embodiments that may be discussed herein, a hydrogel formed using a reaction mixture comprising 5% w/v of a first polymer, 5% w/v of a second polymer 0.1 mg/ml of a polymeric antimicrobial material and 1 mM of an antioxidant material may give rise an antimicrobial material with superior effects, as described hereinbelow. For example, in the above embodiments, the first polymer may be poly(ethylene glycol) tetra thiol, the second polymer may be poly(ethylene glycol) tetra maleimide, the polymeric antimicrobial material may be a polyimidazolium polymer terminated by two maleimide groups and the antioxidant material may be N-acetyl cysteine. Details of how to form the hydrogel described above are provided below.

The hydrogel described herein may be provided in any suitable form to meet the desired type of application. For example, the hydrogel may be provided in the form of a film, nanoparticles or microparticles.

The hydrogel may be used as part of a composite material. Thus, in a further aspect of the invention, there is provided a composite material comprising a substrate and a coating formed of a hydrogel as described hereinbefore. In certain embodiments, the substrate may be a foam.

The hydrogel discussed above may be formed using Click chemistry, thereby enabling potential in situ formation of the desired hydrogel at a site of action on a subject. Thus, there are various kits of parts disclosed herein. For example, the kits may or may not contain an antioxidant material. As such, in a further aspect of the invention, there is disclosed a kit of parts selected from:
- (ai)
  - (aia) a first mixture comprising a first polymer capable of crosslinking with a second polymer;
  - (aib) a second mixture comprising a second polymer and a polymeric antimicrobial material capable of crosslinking with the first polymer; and
  - (aic) a pharmaceutically acceptable solvent; or
- (aii) (aiia) a first mixture comprising a first polymer capable of crosslinking with a second polymer, and a polymeric antimicrobial material capable of crosslinking with the second polymer;
  - (aiib) a second mixture comprising a second polymer; and
  - (aiic) a pharmaceutically acceptable solvent; or
- (aiii) (aiiia) a first mixture comprising a first polymer capable of crosslinking with a second polymer;
  - (aiiib) a second mixture comprising a second polymer;
  - (aiiic) a pharmaceutically acceptable solvent; and
  - (aiiid) a polymeric antimicrobial material capable of crosslinking with the first and second polymers.

In alternative embodiments of the same aspect, but where an antioxidant material is present, there is also disclosed a kit of parts selected from:
- (bi)
  - (bia) a first mixture comprising a first polymer capable of crosslinking with a second polymer and an antioxidant material as described hereinbefore;
  - (bib) a second mixture comprising a second polymer and a polymeric antimicrobial material capable of crosslinking with the first polymer; and
  - (bic) a pharmaceutically acceptable solvent; or
- (bii) (biia) a first mixture comprising a first polymer capable of crosslinking with a second polymer, a polymeric antimicrobial material capable of crosslinking with the second polymer, and an antioxidant material as described hereinbefore;
  - (biib) a second mixture comprising a second polymer; and
  - (biic) a pharmaceutically acceptable solvent; or
- (biii) (biiia) a first mixture comprising a first polymer capable of crosslinking with a second polymer and a polymeric antimicrobial material capable of crosslinking with the second polymer;
  - (biiib) a second mixture comprising a second polymer and an antioxidant material as described hereinbefore; and
  - (biiic) a pharmaceutically acceptable solvent; or
- (biv) (biva) a first mixture comprising a first polymer capable of crosslinking with a second polymer and an antioxidant material as described hereinbefore;
  - (bivb) a second mixture comprising a second polymer;
  - (bivc) a pharmaceutically acceptable solvent; and
  - (bivd) a polymeric antimicrobial material capable of crosslinking with the first and second polymers.

When used herein, the term "pharmaceutically acceptable solvent" is intended to refer to a solvent that may be administered to the body of a subject. For example, the solvent may be water.

The terms "subject", "subjects", "patient" and "patients" include references to mammalian (e.g. human) patients. As used herein the terms "subject" or "patient" are well-recognized in the art, and, are used interchangeably herein to refer to a mammal, including dog, cat, rat, mouse, monkey, cow, horse, goat, sheep, pig, camel, and, most preferably, a human. In some embodiments, the subject is a subject in need of treatment or a subject with a disease or disorder. However, in other embodiments, the subject can be a normal subject. The term does not denote a particular age or sex. Thus, adult and newborn subjects, whether male or female, are intended to be covered.

As will be appreciated, the kit of parts will contain starting materials capable of generating the hydrogels described hereinbefore. Thus, the first polymer and the second polymer mentioned herein correspond to the first polymeric component and the second polymeric component, respectively, and refer to the uncrosslinked materials used to form the hydrogels mentioned herein. Given this, the materials used as the first and second polymers can be readily derived from the information provided hereinbefore.

In the kit of parts described above, the first and second polymers may be selected from one of the following sets:
- (aa) the first polymer may be a polymeric material comprising at least two thiol functional groups and the second polymer may be a polymeric material comprising at least two maleimide groups;
- (bb) the first polymer may be a polymeric material comprising at least two thiol functional groups and the second polymer may be a polymeric material comprising at least two vinyl sulfone groups;
- (cc) the first polymer may be a polymeric material comprising at least two azide functional groups and the second polymer may be a polymeric material comprising at least two cyclooctynyl groups;
- (dd) the first polymer may be a polymeric material comprising at least two amine functional groups and the second polymer may be a polymeric material comprising at least two aldehyde groups; and
- (ee) the first polymer may be a polymeric material comprising at least two amine functional groups and the second polymer may be a polymeric material comprising at least two acrylate groups.

In the kit of parts described above, the first polymer may be a polymeric material comprising at least two thiol functional groups and the second polymer may be a polymeric material comprising at least two maleimide groups, optionally wherein:
- (ff) the first polymer may be a polymeric material that has from 2 to 8 thiol functional groups and the second polymer may be a polymeric material that has from 2 to 8 maleimide groups;
- (gg) the first polymer may be a multi-arm polyethylene glycol having from 2 to 8 arms that are each terminated by a thiol functional group and the second polymer may be a multi-arm polyethylene glycol having from 2 to 8 arms that are each terminated by a maleimide group;
- (hh) the first polymer may be poly(ethylene glycol) tetra thiol and the second polymer may be poly(ethylene glycol) tetra maleimide.

In the kit of parts described above, the polymeric antimicrobial material capable of crosslinking with the first and/or second polymers may be selected from those described above. Similarly, when present, the antioxidant material may be selected from those disclosed hereinbefore.

As will be appreciated, the hydrogel described herein may be suitable for use in medicine. Thus in a further aspect of the invention, there is provided the use of a hydrogel as described herein in the manufacture of a medicament for wound healing. There is also provided a method of wound healing comprising applying a hydrogel as described herein to a subject in need thereof.

As noted hereinbefore, the hydrogel described herein may be formed in situ at the site of a wound on a subject. This may have advantages in ensuring that the resulting hydrogel closely conforms to the wound in question and may reduce or eliminate problems associated with the storage (e.g. over extended periods of time) and transportation of hydrogels containing active ingredients. Such problems may include, but are not limited to degradation of the hydrogel and/or the active ingredients. Other problems that may be solved include avoiding premature cleavage of the active ingredients from the hydrogel resulting in a burst phase on use, which reduces the overall effectiveness of the hydrogel.

The hydrogels disclosed herein may be formed by any suitable method. For example, the hydrogel may be formed by forming solutions of the first and second mixtures (as described above in relation to the kit of parts) and, if present, any separate components (e.g. a polymeric antimicrobial material capable of crosslinking with the first and second polymers) and then mixing the resulting solutions together to generate the desired hydrogel containing the desired active ingredients. Further details of how said methodology works are provided in the examples section below.

Thus, in an aspect of the invention, there is provided a method of forming a hydrogel as described herein, comprising the steps of:

(AA) providing at least two separate solutions, each of said solutions containing a solvent, where each of the at least two solutions contain one or more of a first polymer capable of crosslinking with a second polymer, a second polymer capable of crosslinking with the first polymer, a polymeric antimicrobial material capable of crosslinking with the first and/or second polymer, and, optionally, an antioxidant material as described herein, provided that materials that can react together are not contained in the same solution; and (BB) mixing the at least two solutions together to form the hydrogel as described herein. As will be appreciated, the at least two solutions mentioned above may be derived from the kits of parts mentioned hereinbefore.

In embodiments that may also be described herein, a foam may be used as a substrate and may be coated with the hydrogels discussed herein. Thus, in a further aspect of the invention, there is disclosed a foam comprising a foam substrate coated with a hydrogel as disclosed herein. Any suitable foam may be used in this aspect. For example, the foam may be a biocompatible foam that may be place onto or into the wound on a subject. The coating of the foam substrate may be accomplished by dipping the foam substrate into the respective solutions mentioned hereinbefore in relation to the kits of parts to form the coating.

The aspects of the invention described herein (e.g. the above-mentioned hydrogels, kits of parts to form said hydrogels, methods and uses) may have the advantage that, in the treatment of the conditions described herein, they may be more convenient for the physician and/or patient than, be more efficacious than, be less toxic than, have better selectivity over, have a broader range of activity than, be more potent than, produce fewer side effects than, or may have other useful pharmacological properties over, other treatment regimens known in the prior art for use in the treatment of those conditions or otherwise.

Further aspects and embodiments of the invention will now be described by the following non-limiting examples.

EXAMPLES

Materials 1,4-diaminobutane, 37% formaldehyde solution, 40% glyoxal solution, acetic acid, maleic anhydride, sodium bicarbonate and N-acetylcysteine (NAC) were purchased from Sigma-Aldrich and used as received. Branched polyethylenimine (PEI, $M_n$=25,000) was purchased from Sigma-Aldrich and lyophilized to dryness before use. Poly(ethylene glycol) tetra thiol (PEG-4SH, $M_n$=20,000) and poly(ethylene glycol) tetra maleimide (PEG-4mal, $M_n$=20,000) were purchased from Biochempeg.

Example 1

The synthesis method and characterizing information for maleimide-terminated polyimidazolium (PIM-mal) are provided below.

PIM-mal was synthesized via the reaction of 1,4-diaminobutane, formaldehyde and glyoxal (Lindner, J. P. *Macromolecules* 2016, 49, 2046-2053), followed by end-functionalization with maleimide (FIG. 1). 1,4-diaminobutane (2.974 g, 33.7 mmol) was dissolved in acetic acid (75 mL) in a round-bottom flask and cooled in an ice bath. 37% formaldehyde solution (2.735 g, 33.7 mmol) and 40% glyoxal solution (4.895 g, 33.7 mmol) were first dissolved in DI water (37.5 mL), then added to the round-bottom flask in a dropwise manner. The solution was stirred at room temperature for 24 h, and the solvents were evaporated completely on a rotary evaporator. The produced polyimidazolium (PIM) was dissolved in DI water and then subjected to dialysis in DI water. The final product was obtained via lyophilization. PIM (2 g, 0.7 mmol) was then dissolved in acetic acid (50 mL) in a round-bottom flask. Maleic anhydride (0.27 g, 2.8 mmol) and sodium bicarbonate (0.24 g, 2.8 mmol) were added to the round-bottom flask and stirred to dissolve the solids completely Then, the solution was stirred at 100° C. for 24 h, and the solvent was evaporated completely on a rotary evaporator. The produced PIM-mal was dissolved in DI water and then subjected to dialysis (MWCO 2000) in DI water for three days. The final product was obtained via lyophilization.

$^1$H NMR (300 MHz, DMSO) δ: 10.31 (C—H), 7.94 (C—H), 6.29 (C—H), 4.29 (—CH$_2$—) 1.79 (—CH$_2$—), 1.59 (CH$_3$COO—). Average molecular weight ($M_n$)=2766 Da (determined by gel permeation chromatography).

Example 2

The minimum inhibitory concentration (MIC) of PIM-mal prepared in Example 1 was tested on various ESKAPE strains of bacteria (*E. faecium* 19434, methicillin-resistant *S. aureus* (MRSA BAA-40 and MRSA USA300), *K. pneumoniae* 13883, carbapenem-resistant *A. baumannii* (CR-AB), *P. aeruginosa* PA01, carbapenem-resistant *P. aeruginosa* (CR-PA) and *E. aerogenes* 13047). The experimental protocol and results of the MIC tests are provided below.

Bacteria (*E. faecium* 19434, MRSA BAA-40, MRSA USA300, *K. pneumoniae* 13883, CR-AB, PA01, CR-PA and *E. aerogenes* 13047) were inoculated and dispersed in Mueller-Hinton broth (MHB, 4 mL) at 37° C. with continuous shaking at 220 rpm to mid log phase. A two-fold serial dilution of PIM-mal was made (1024 µg/mL to 2 µg/mL in 50 µL MHB) on a 96-well plate. Then, bacterial suspension (50 µL) was added to all the wells that contained PIM-mal to a final concentration of $5 \times 10^5$ CFU/mL. The plate was then incubated in a shaker at 37° C. for 18 h and the optical density of the wells were measured to determine the MIC.

Results and Discussion

The MIC of PIM-mal for the tested bacteria varies from 2 to 8 µg/mL and is shown in Table 1. The results indicate that PIM-mal is potent in inhibiting the growth of a wide number of strains of bacteria.

TABLE 1

Minimum inhibitory concentration (MIC) of PIM-mal against various ESKAPE bacteria.

| MIC (µg/mL) | *E. faecium* 19434 | MRSA BAA-40 | MRSA USA300 | *K. pneumoniae* 13883 |
| --- | --- | --- | --- | --- |
| PIM-mal | 4 | 2 | 4 | 8 |

| | CR-AB | PA01 | CR-PA | *E. aerogenes* 13047 |
| --- | --- | --- | --- | --- |
| | 8 | 4 | 8 | 4 |

Example 3

A series of hydrogel formulations were prepared with poly(ethylene glycol) tetra thiol (PEG-4SH, 5% w/v), poly(ethylene glycol) tetra maleimide (PEG-4mal, 5% w/v), antibacterial PIM-mal (0.1, 1 or 10 mg/mL) and antioxidative NAC (1 mM) in DI water (Table 2) and the protocol is described in detail below. The hydrogel precursors react by crosslinking via specific and efficient thiol-maleimide Michael Addition reaction at near neutral pH (7.2-7.6) (Nair, D. P. et al., *Chem. Mater.* 2013, 26, 724-744; and Martínez-Jothar, L. et al., *J. Control. Release* 2018, 282, 101-109) to form the antibacterial and antioxidative hydrogels.

The hydrogels were formed by simply mixing the precursor solutions. Firstly, the two-component solutions were prepared. One solution contained PEG-4SH (10% w/v) and NAC (2 mM) in DI water while the other solution contained PEG-4mal (10% w/v) and PIM-mal (0.2, 2 or 20 mg/mL) in DI water. These solutions were mixed at equal volume in a 1.5 mL microtube and 50 µL of the hydrogel solution was quickly transferred to each well of a 96-well plate. The final hydrogel solution contained 5% PEG-4SH, 5% PEG-4mal, 1 mM NAC and 0.1, 1 or 10 mg/mL PIM-mal. The solutions were then left on the bench for 5 min to gel. DI water was added to the wells to swell the hydrogels. The hydrogels were then washed in ethanol thrice and in DI water with sonication thrice, to remove all unreacted precursors. A gel control was made by mixing PEG-4SH (5% w/v) and PEG-4mal (5% w/v) in DI water without the active components (denoted as PPcontrol) for use as a comparison.

TABLE 2

PPN hydrogel formulations.

| Hydrogel formulations | PEG-4SH | PEG-4mal | PIM-mal | NAC |
| --- | --- | --- | --- | --- |
| PPcontrol | 5% | 5% | — | — |
| PPN0.1 | 5% | 5% | 0.1 mg/mL | 1 mM |
| PPN1 | 5% | 5% | 1 mg/mL | 1 mM |
| PPN10 | 5% | 5% | 10 mg/mL | 1 mM |

The hydrogel precursors were able to crosslink in DI water in less than one minute. The hydrogel network is mainly made up of PEG-4SH and PEG-4mal, while NAC and a portion of the PIM-mal are tethered to the network as pendant molecules. These hydrogels are termed PEG-PIM-NAC (PPN) and are named according to their PIM-mal concentration of 0.1, 1 and 10 mg/mL as PPN0.1, PPN1 and PPN10 respectively. Indeed, this method of fabricating the hydrogels allows for different concentrations of the active components (PIM-mal and NAC) to be grafted onto the hydrogel to treat infected wounds of different severities.

Example 4

The in vitro contact killing efficacies of the hydrogels prepared in Example 3 were measured against various multi-drug resistant (MDR) Gram-negative and Gram-positive bacteria, specifically strains that are relevant in wound infections (*S. aureus, P. aeruginosa* and *A. baumannii*) (KirkupJr, B. C. *Adv Wound Care* (*New Rochelle*) 2015, 4, 12-23). The in vitro antimicrobial assay protocol and experimental results are provided below.

(1) Preparation of Bacterial Suspensions

Bacteria (MRSA USA300, CR-AB, PA01 and CR-PA) were inoculated and dispersed in Mueller-Hinton broth (MHB, 4 mL) at 37° C. with continuous shaking at 220 rpm to mid log phase. The MHB was removed by centrifugation, followed by decanting of the supernatant. The bacteria were washed with phosphate buffered saline (PBS) thrice and the final bacteria suspensions were prepared with PBS (1 mL, $1 \times 10^9$ CFU/mL).

(2) Inoculation of Bacteria on Hydrogels

The bacterial suspension in PBS (10 µL), containing approximately $1 \times 10^7$ CFU was inoculated and spread evenly onto the surface of hydrogels, which were placed on a small petri dish. A control was prepared by inoculating bacteria on a small petri dish with no hydrogel. The hydrogels were incubated at 37° C. for 1 h with 90% relative humidity.

(3) Bacterial Counts

The hydrogels were immersed in PBS (1 mL) and vortexed to release bacteria. Then, a series of ten-fold dilutions of the bacterial suspensions were prepared in a 96-well plate and dilutions were plated onto Luria-Bertani (LB) agar. The plates were incubated at 37° C. for 16 h and bacterial colonies were counted.

The results were evaluated as follows (Equation 1):

$$\text{Log reduction} = \text{Log(total } CFU \text{ of control)} - \text{Log(total } CFU \text{ on hydrogels)} \quad (1)$$

Results and Discussion

PPN1 and PPN10 totally eradicated the various bacteria loaded onto the hydrogel discs in just 1 h (Table 3). The bacteria eradicated include methicillin-resistant *S. aureus* (MRSA USA300), *P. aeruginosa* PA01, and carbapenem-resistant Gram-negative *P. aeruginosa* and *A. baumannii* strains (CR-PA and CR-AB), which are pathogens of great concern worldwide (Dunnill, C. et al., *Int. Wound J.* 2017, 14, 89-96; and World Health Organization (2017, February 27). WHO publishes list of bacteria for which new antibiotics are urgently needed). On the other hand, PPN0.1 hydrogel did not completely eradicate the bacteria (Table 3). This is probably due to the lower concentration of the active antibacterial PIM-mal tethered to the hydrogel. The gel control, PPcontrol, did not exhibit bactericidal properties.

TABLE 3

In vitro bacterial log reductions of the PPN hydrogels against various clinically relevant bacteria strains.

| c) Hydrogel bactericidal activity | MRSA USA300 Log reduction | CR-AB Log reduction | PA01 Log reduction | CR-PA Log reduction |
|---|---|---|---|---|
| PPcontrol | 0.05 | 0.03 | 0.04 | 0.02 |
| PPN0.1 | 3.15 | 2.97 | 2.76 | 3.09 |
| PPN1 | 7.20* | 7.37* | 7.06* | 7.19* |
| PPN10 | 7.20* | 7.37* | 7.06* | 7.19* |

*denotes that no bacterial colonies were observed on the agar plate after incubation for 16 h. The initial bacterial inoculum was approximately $1 \times 10^7$ CFU per sample.

Example 5

The biocompatibility studies of PIM-mal and PPN hydrogel extracts prepared in Examples 1 and 3, respectively, were carried out in vitro on human dermal fibroblasts (NHDF-Ad-Der Fibroblasts, CC2511, Lonza). Fully supplemented DMEM, consisting of fetal bovine serum (FBS, 10%) and antibiotics (penicillin-streptomycin, 1%) was used as the cell culture medium. The in vitro biocompatibility assay protocol for each material is described below.

PIM-Mal MTT Assay

HDF cells were cultured in 96-well plates from an initial density of $1 \times 10^4$ cells in each well, and incubated in a $CO_2$ incubator at 37° C. for 24 h for cell attachment. Different concentrations of PIM-mal (0.1, 0.2, 0.3, 0.5 and 1 mg/mL) were prepared in DMEM and added to the wells and incubated at 37° C. for a further 24 h. Then, the culture media were replaced with MTT solution (1 mg/mL in DMEM) and incubated at 37° C. for 4 h to stain viable cells. The MTT solution was discarded, dimethyl sulfoxide (DMSO) was added and mixed well. The cell viability was calculated based on the absorbance of each well at 570 nm against the cell-only control wells which served as the 100% cell viability control.

Hydrogel Extract MTT Assay

HDF cells were cultured in 24-well plates from an initial density of $5 \times 10^4$ cells in each well, and incubated in a $CO_2$ incubator at 37° C. for 24 h for cell attachment. Concurrently, hydrogels were placed in each well of a 24-well plate with 1 mL of DMEM and incubated at 37° C. for 24 h to collect the extracts, before transferring the extracts to incubate with HDF cells at 37° C. for 24 h. Then, the culture media were replaced with MTT solution and subsequent steps were the same as above.

Contact MTT Assay

The procedure is as described above, but instead of collecting hydrogel extracts, the hydrogels were directly immersed in the cell cultures and removed before addition of MTT.

The results were evaluated as follows (Equation 2):

$$\text{Cell viability}(\%) = \frac{\text{Absorbance of polymer/hydrogel treated cells}}{\text{Absorbance of control cells}} \times 100\% \quad (2)$$

Results and Discussion

Figure 2:
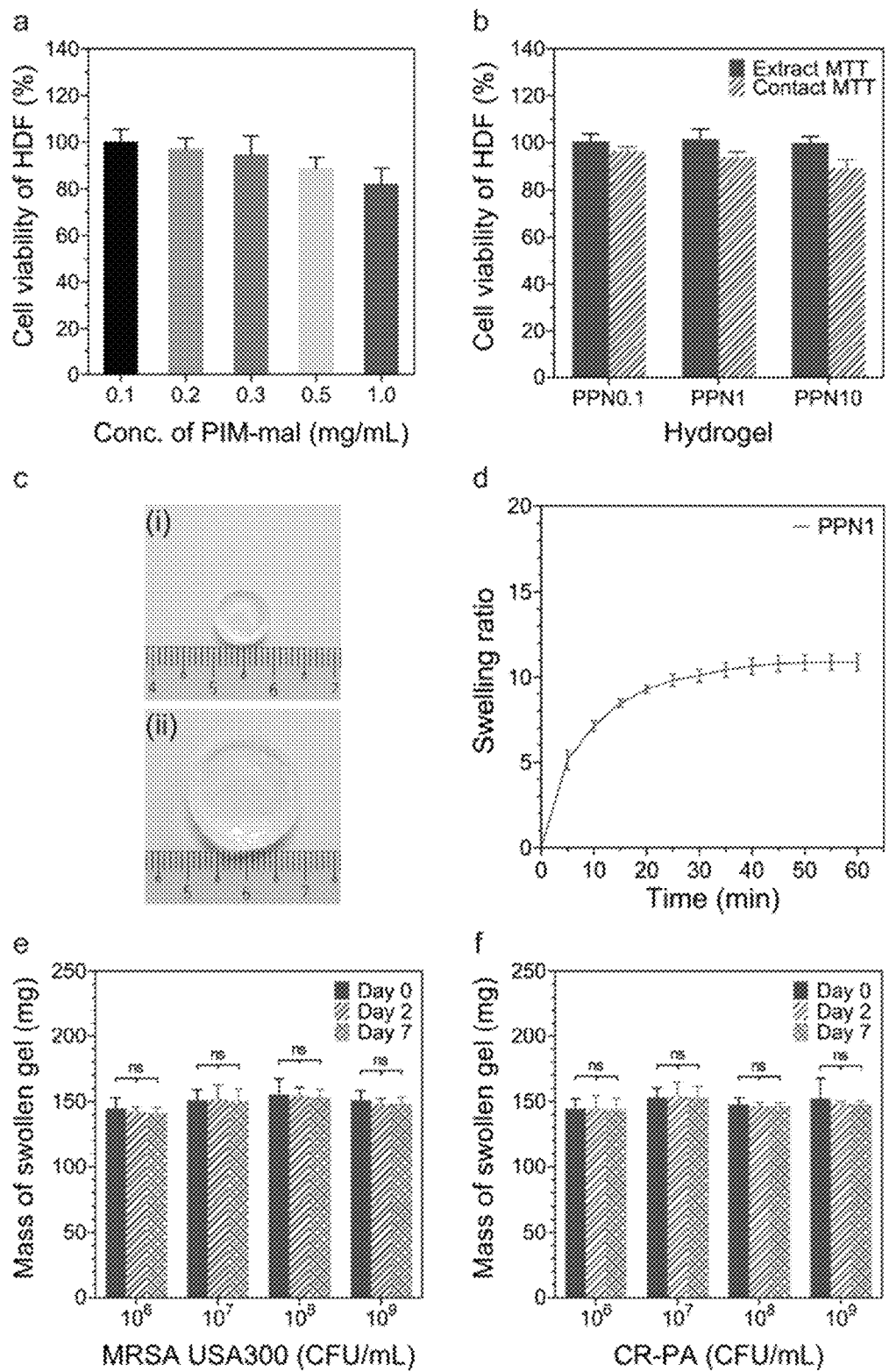
FIG. 2 shows the in vitro characterizations of PIM-mal and PPN hydrogels. (a) Cell viability of human dermal fibroblasts (HDF) when incubated with different concentrations of PIM-mal solution for 24 h (n=3); (b) Cell viability of HDF when incubated for 24 h with various PPN hydrogels using hydrogel extract and contact MTT assays (n=3); (c) Visual appearance and size of PPN1 hydrogels fabricated in (i) 96-well plate and (ii) 24-well plate; (d) Swelling ratio (mass increase/initial mass) against time of PPN1 hydrogel (n=3), and mass of swollen PPN1 hydrogels when incubated with extracts of (e) MRSA USA300; and (f) CR-PA for 2 and 7 days (n=3).

The PIM-mal polymer is relatively non-cytotoxic even at a high concentration of 1 mg/mL as the viability of HDF was above 81% (FIG. 2a). The cell viability of HDF was 100% for all the hydrogel extracts (FIG. 2b). For the hydrogel contact MTT assay, the cell viabilities were 97%, 94% and 89% for PPN0.1, PPN1 and PPN10 respectively (FIG. 2b), indicating low acute toxicity of these hydrogels. This good biocompatibility is due to biocompatible hydrogel precursors, efficient thiol-maleimide cross-linking, extensive washing and high hydration of the charged hydrogel. The PPN1 and PPN10 hydrogels (Table 2) showed similarly high in vitro bacterial killing and good biocompatibility. Therefore, PPN1 was chosen for further characterizations as it contains a lower concentration of PIM-mal.

Example 6

The swelling kinetics and stability of PPN1 (prepared in Example 3) in bacterial extracts were evaluated as described below.

Swelling Kinetics of Hydrogels

The hydrogels were washed thoroughly and lyophilized to dryness. The masses of fully dried hydrogels were weighed at time zero. Then, a copious amount of DI water was added to the hydrogels to induce swelling. At 5 min intervals until equilibrium swelling, the hydrogels were removed from the water, dried with filter paper, and their masses were measured. The hydrogels were then returned to their respective water baths to continue swelling. The swelling ratio was calculated using the formula (Equation 3):

$$\text{Swelling ratio} = \frac{\text{mass of hydrogel at } n^{th} \text{ min} - \text{initial mass of hydrogel}}{\text{initial mass of hydrogel}} \quad (3)$$

Hydrogel Stability in Bacterial Extracts

Bacterial extracts were prepared by shaking different concentrations of bacteria in PBS at 37° C. for 24 h. Extracts were collected after centrifugation and removal of the bacteria. PPN1 hydrogels were placed in a 24-well plate and equilibrated by soaking in PBS for 24 h. Their initial mass was measured. Each hydrogel was then incubated with bacterial extract (1 mL) at 37° C. for 2 and 7 days and their masses were measured at the respective days.

Results and Discussion

The PPN1 hydrogel is transparent (FIG. 2c) and swells significantly and rapidly in water as the PPN1 hydrogel swelled to an equilibrium of 10.9× its dry weight within 50 min of immersion in water (FIG. 2d). The PPN1 hydrogel were stable when incubated with bacterial extracts of MRSA USA300 and CR-PA for 2 and 7 days, and showed almost constant mass throughout these time periods (FIGS. 2e and 2f). The slight variation (but non-significant) of its mass was due to dynamic swelling of hydrogel which is affected by temperature, pH and chemical potential of the solution (Curatolo, M. et al., *J. Appl. Phys.* 2017, 122, 145109; Alegre-Requena, J. V. et al., *J. Mater. Chem. B.* 2019, 7, 1652-1673; and Chen, S. et al., *J. Chem. Phys.* 2018, 149, 094904). These results proved that PPN1 hydrogel is resistant to degradation by bacterial extracts.

Example 7

An in vitro human skin equivalent (HSE) model was done using de-epidermised dermis (DEDs) to investigate the in vitro keratinocyte growth (measured by MTT staining) over 7 days of PPN1 hydrogel (prepared in Example 3) treatment in a simulated wound made on the DEDs. The experimental protocol and results are provided below.

DEDs were placed in 24-well plates and a sterile ring was placed on top of each DED and gently pressed against the DED to create a seal. 600 μL of full green medium was filled on the outside of each ring. Then, $2 \times 10^4$ keratinocytes in 100 μL of full green medium were seeded into the centre of each ring and incubated for 48 h. The DEDs were then transferred onto metal grids in 6-well plates filled with full green media to create an air-liquid interface for 9 days. When the epidermal layers were formed on the DEDs, 4 mm superficial excisional wounds were created on the DEDs with a 4 mm biopsy punch. Treatments were applied on the DEDs for 7 days, after which they were removed and the DEDs were stained with MTT. The DEDs were then sectioned and sent for H&E staining and imaging.

Results and Discussion

Figure 3:
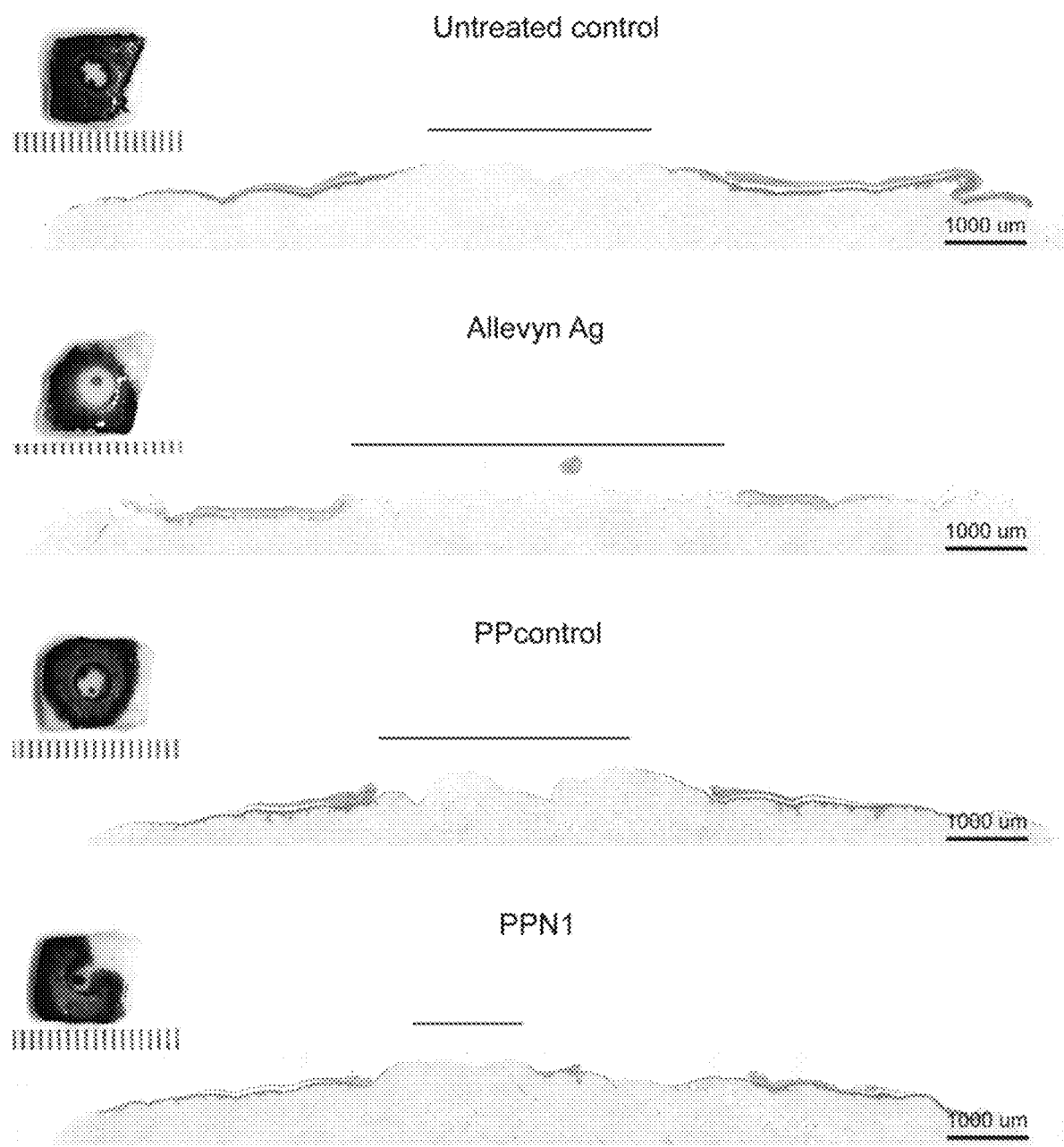
FIG. 3 depicts the in vitro human skin equivalent (HSE) model. Images of the DEDs that are stained with MTT after various treatments for 7 days, and their corresponding H&E images. The straight lines represent the unepithelized part of the DEDs.
Figure 4:
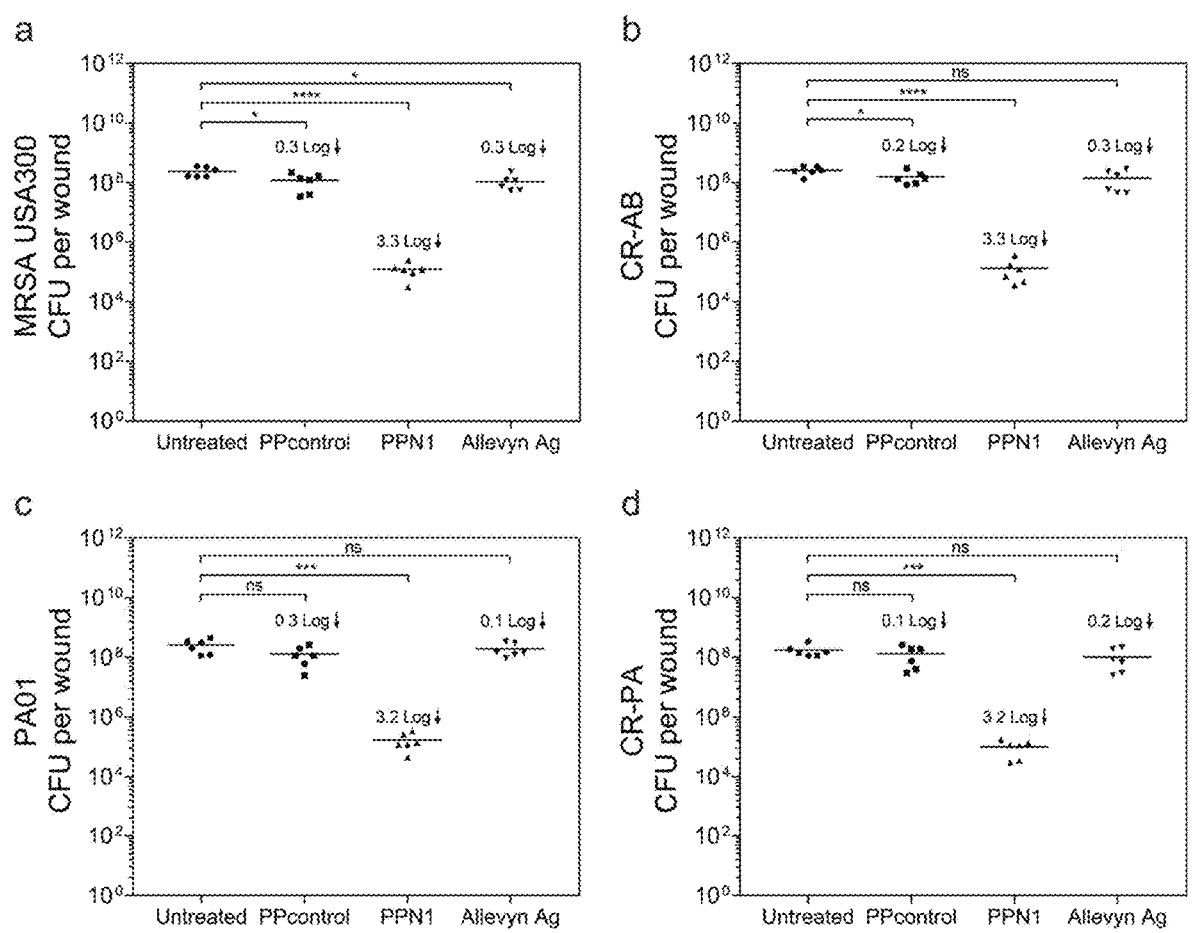
FIG. 4 depicts the mouse in vivo diabetic wound infection model with 24 h post-infection treatment. Bacterial counts of (a) MRSA USA300; (b) CR-AB; (c) PA01; and (d) CR-PA on various treated and control wounds after one day (n=6). * denotes P<0.05, * denotes P<0.001 and ** denotes P<0.0001.

It was discovered that PPN1 hydrogel caused the keratinocytes to proliferate into the simulated wound faster than the PPcontrol or in the untreated control (FIG. 3). A commercial silver-based antimicrobial wound dressing (Allevyn Ag from Smith & Nephew) used as a comparison did not show any keratinocyte growth at all (FIG. 3). Therefore, the H&E images done on the DEDs supported our findings that PPN1 hydrogel promoted keratinocyte growth to form the epidermis quicker than other treatments (FIG. 3).

Example 8

The in vivo bactericidal activities of PPN1 hydrogel (prepared in Example 3) against clinically relevant Gram-negative and Gram-positive bacteria were tested with a murine excisional diabetic wound infection model using MRSA USA300, CR-AB, PA01 and CR-PA, and were compared with Allevyn Ag. The experimental protocol and results are provided below.

All animal studies were approved and performed in compliance with the regulations of the Institutional Animal Care and Use Committee of Nanyang Technological University.

(1) Induction of Diabetic Mice Using Streptozotocin

Eight-week old male C57BL/6 mice were used. Streptozotocin (STZ) solution was prepared by dissolving the powder in 50 mM sodium citrate buffer to 4 mg/mL. Mice were fasted for 4 h before injecting STZ intraperitoneally at 40 mg/kg daily for five consecutive days. 10% sucrose water was provided during the injection days and was changed to regular water on day 6. Blood glucose levels of the mice were measured three weeks after STZ injection and the mice were deemed to be diabetic if their blood glucose level exceeded 11.1 mmol/L.

(2) Wound Infection Models and Enumeration of Bacterial Load on Wounded Skin

Mice were anaesthetized, depilated and 6 mm diameter full-thickness excisional wounds were inflicted on the dorsal skin and the underlying *panniculus carnosus* as previously described (Tan N. S. et al., *Curr Protoc Mouse Biol* 2013, 3, 171-185). Next, bacteria (MRSA USA300, CR-AB, PA01 and CR-PA, $1 \times 10^6$ CFU in 10 μL of PBS) were topically inoculated onto the wounds and left to settle for 10 min prior to securing with Tegaderm (3M) transparent dressing. The bacteria were left untreated on the wounds for 24 h to form biofilm. The wounds were then treated with PPcontrol, PPN1 hydrogel and Allevyn Ag to stimulate an anti-biofilm treatment. Untreated wounds served as controls. The dressings were removed after 24 h and the wounds, including 5 mm of the peripheral region, were excised. Each wound was homogenized in PBS (900 μL) to release bacteria (n=6). Then, a series of ten-fold dilutions of bacterial suspension was done in PBS and plated on LB agar. The plates were incubated at 37° C. for 16 h and bacterial colonies were counted. A two-tailed Student's t test was used for comparisons.

Results and Discussion

Figure 5:
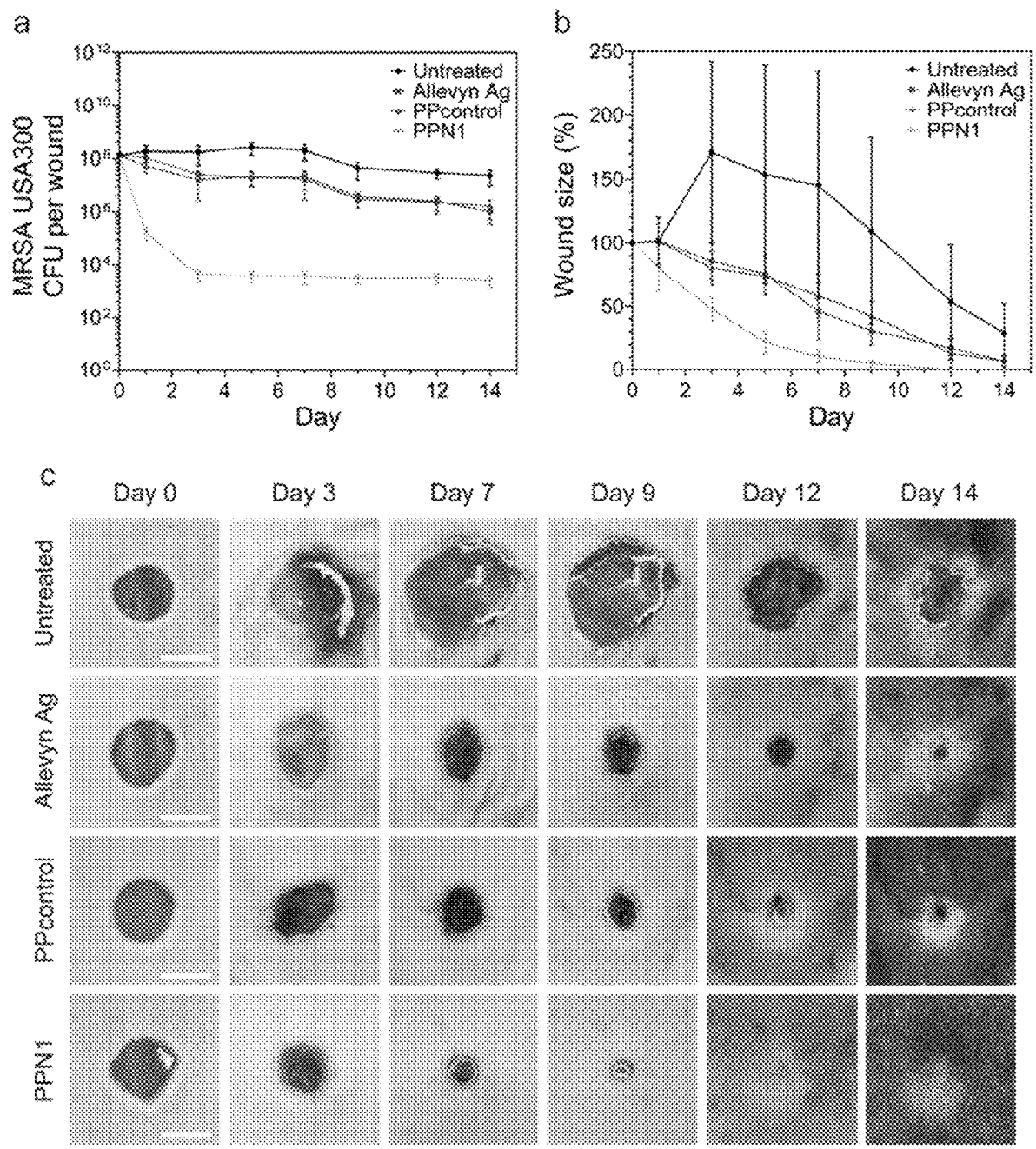
FIG. 5 depicts the full wound healing study. (a) Bacterial counts of MRSA USA300 on various treated and control wounds on days 0, 1, 3, 5, 7, 9, 12 and 14 (n=6); (b) Wound sizes of untreated control, and Allevyn Ag, PPcontrol and PPN1 hydrogel-treated wounds on various days as a percentage of the initial wound size (n=6); and (c) Visual appearance of representative untreated control, and Allevyn Ag, PPcontrol and PPN1 hydrogel-treated wounds between dressing changes. Scale bar=5 mm.

In the anti-biofilm treatment model, PPN1 hydrogel showed greater than 3 log reduction (>99.9%) for all tested bacterial strains (FIGS. 4*a*-*d*). This is superior to the generally ineffective treatments (0.1-0.3 log reduction) with Allevyn Ag and the PPcontrol (FIGS. 4*a*-*d*). Hence, the PPN1 hydrogel is broad spectrum and significantly kills (>3 log reduction) the MDR biofilm bacteria tested, which the Ag-based Allevyn dressing did not. We also studied the dynamics of biofilm bacteria (MRSA USA300) reduction at the wound site over a period of 2-weeks treatment with the different dressings (FIG. 5*a*). Most of the reduction in wound bacteria occurred during the first three days of treatment with PPN1 hydrogel, after which bacterial counts remained almost constant, at about $10^{-4}$ of the initial count (FIG. 5*a*). Allevyn Ag and PPcontrol removed much less bacteria and the untreated control produced barely any reduction of bacteria over 2 weeks (FIG. 5*a*). Therefore, our PPN1 hydrogel is more bactericidal to biofilm bacteria than the commercial silver-based wound dressing Allevyn Ag, even to CR-PA and CR-AB which urgently need new antibacterial therapies (World Health Organization (2017, February 27). WHO publishes list of bacteria for which new antibiotics are urgently needed).

The PPN1 hydrogel absorbs bacteria into its pore spaces due to hydrodynamic drag force, followed by contact killing of the bacteria, away from the wound site, on the cationic hydrogel pore walls. Then, thiol substitution by free thiols (mainly glutathione, GSH) present in wound tissues causes NAC and singly-attached PIM to dissociate away from the hydrogel network into the wound site. As a result, solution PIM can exert its antibacterial effects to kill more bacteria in the wound site.

Example 9

The stability of PPN1 hydrogel (prepared in Example 3) was tested on infected wound and in wound fluids as described below.

PPN1 Hydrogel Stability after Treatment on Infected Wound

PPN1 hydrogel images were taken before and after treatment on MRSA USA300-infected wounds on the dorsal skin of mice. The wound infection procedures were carried out as described in Example 8.

Stability of PPN1 Hydrogel in Wound Fluids

Wound fluids of MRSA USA300- and CR-PA-infected wounds were prepared by homogenizing tissue from one wound in 900 µL of PBS, followed by 10× dilution in PBS (total volume=10 mL) (Note: When the wound tissue is homogenized in PBS, it contributes approximately 100 µL to the PBS solution, making it 1 mL (900 µL from PBS and 100 µL from wound tissue). Therefore, the total volume after 10× dilution in PBS will be 10 mL. The wound fluid supernatants were collected after centrifugation and removal of the tissues. PPN1 hydrogels were placed in a 24-well plate and equilibrated by soaking in PBS for 24 h. Their initial masses were measured. Each hydrogel was then incubated with wound fluid (1 mL) at 37° C. for 2 and 7 days and their masses were measured at the respective time points.

Results and Discussion

Figure 6:
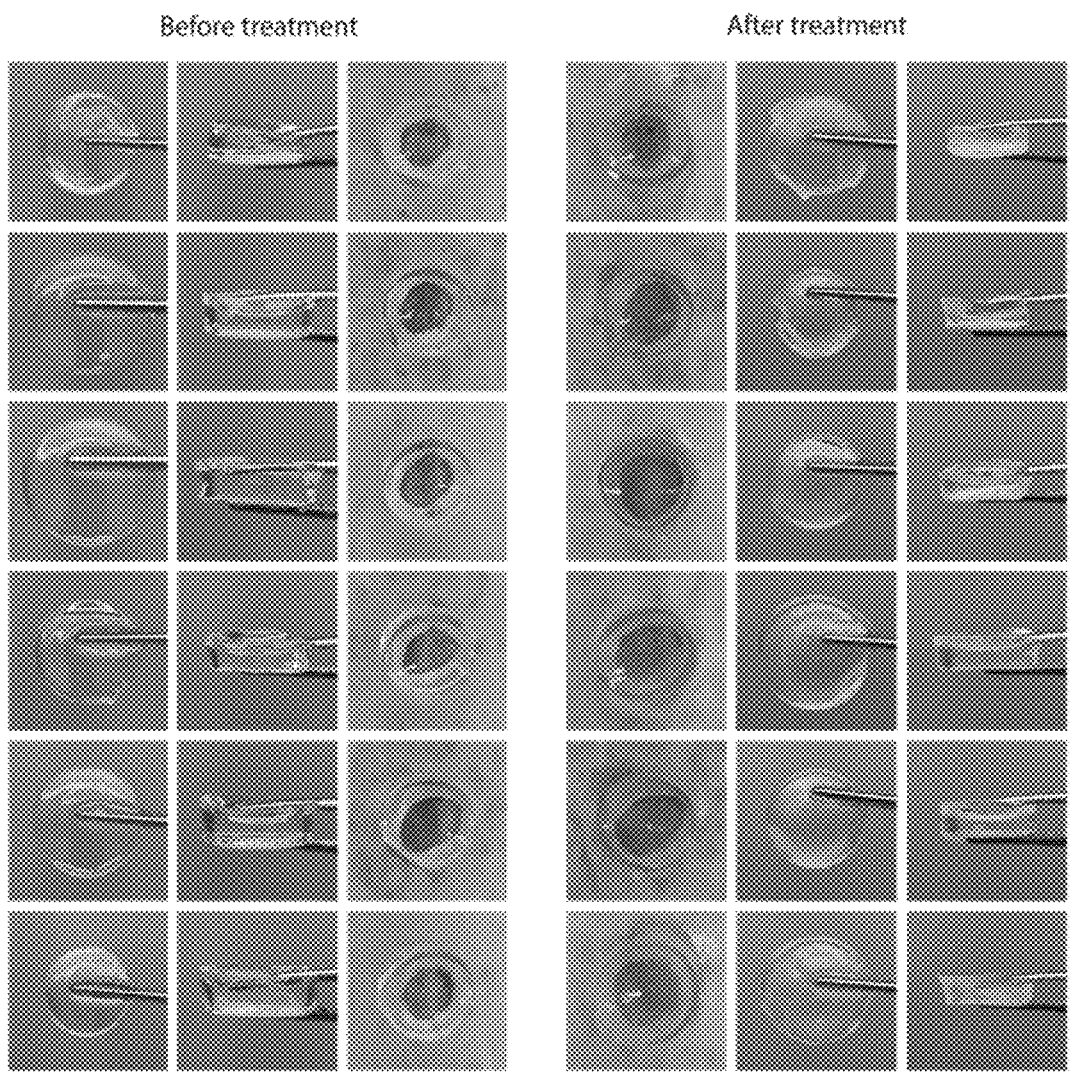
FIG. 6 shows the PPN1 hydrogel images before (left) and after (right) 2 days of treatment on MRSA USA300-infected wounds.
Figure 7:
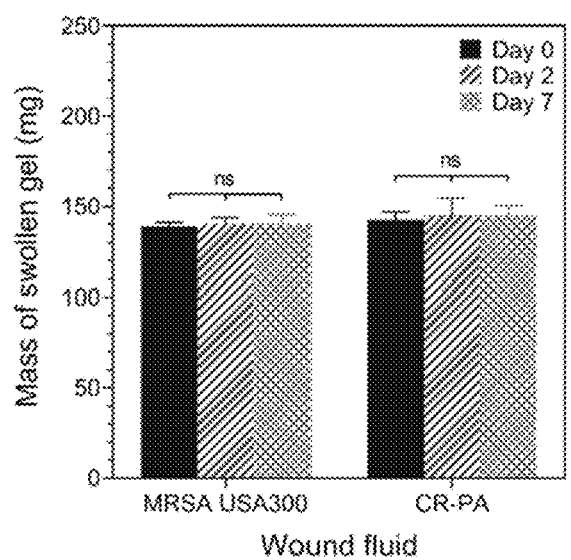
FIG. 7 shows the mass of swollen PPN1 hydrogels when incubated with wound fluids of MRSA USA300- and CR-PA-infected wounds for 2 and 7 days (n=3).
Figure 8A:
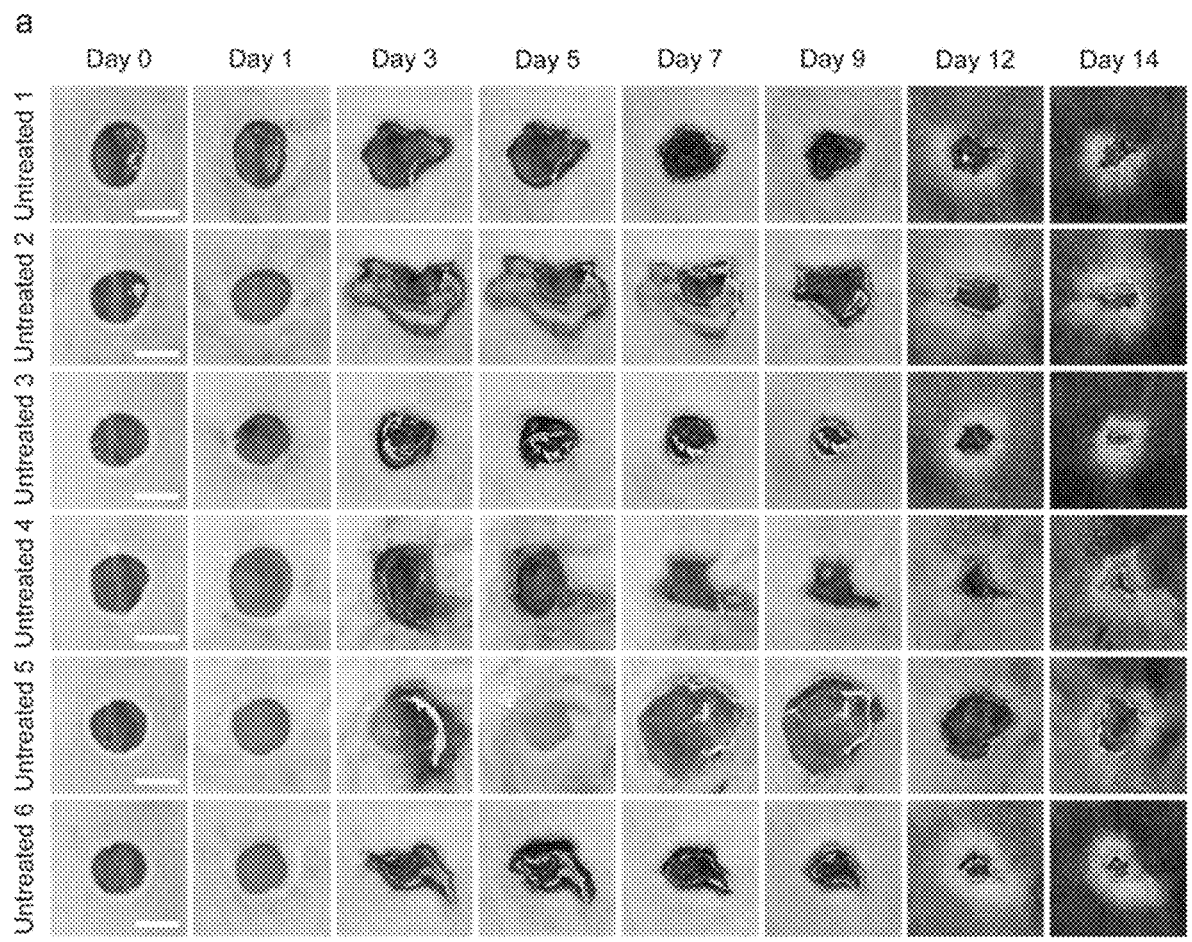
FIG. 8A-D depicts the wound healing study. (A) Visual appearance of untreated control wounds between dressing changes over 2 weeks. Scale bar=5 mm; (B) Visual appearance of Allevyn Ag treated wounds between dressing changes over 2 weeks. Scale bar=5 mm; (C) Visual appearance of PPcontrol treated wounds between dressing changes over 2 weeks. Scale bar=5 mm; and (D) Visual appearance of PPN1 treated wounds between dressing changes over 2 weeks. Scale bar=5 mm.
Figure 8B:
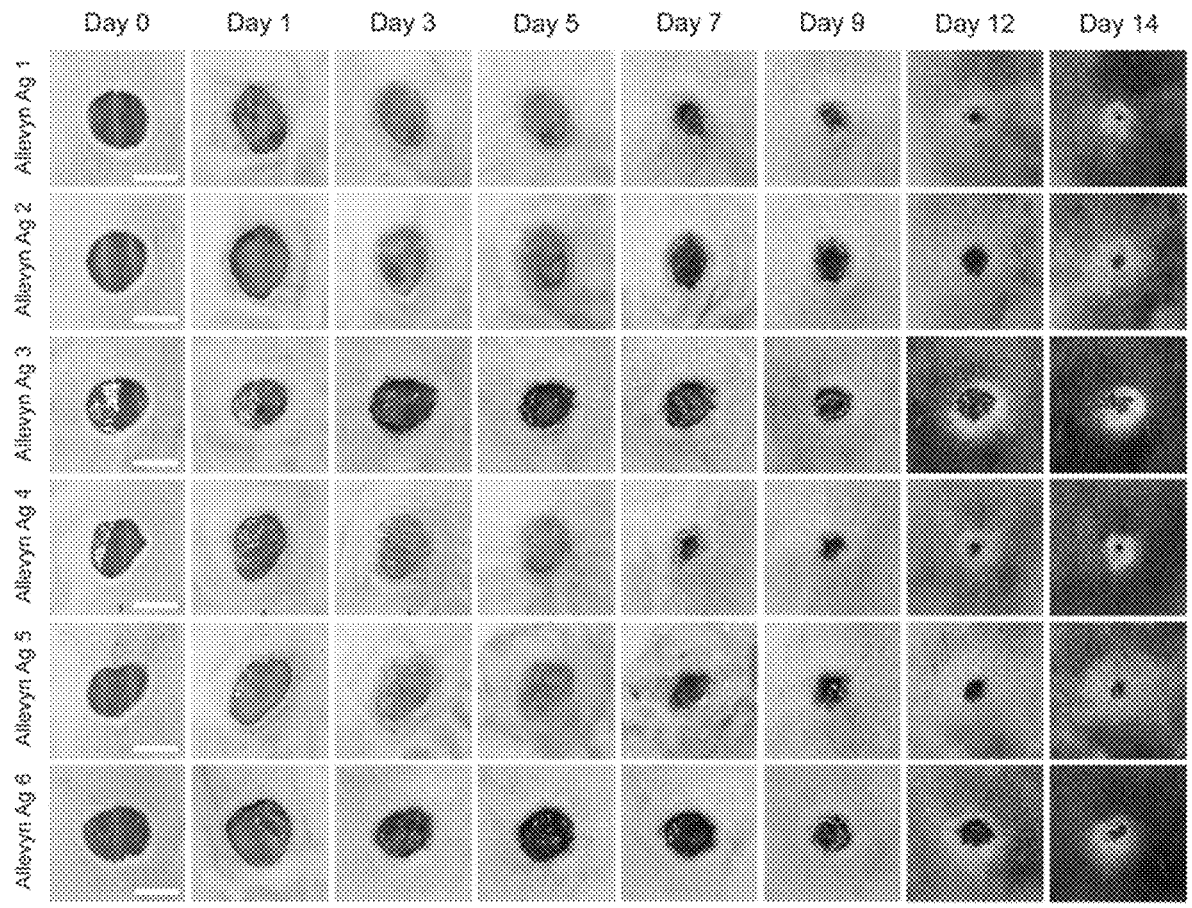
Figure 8C:
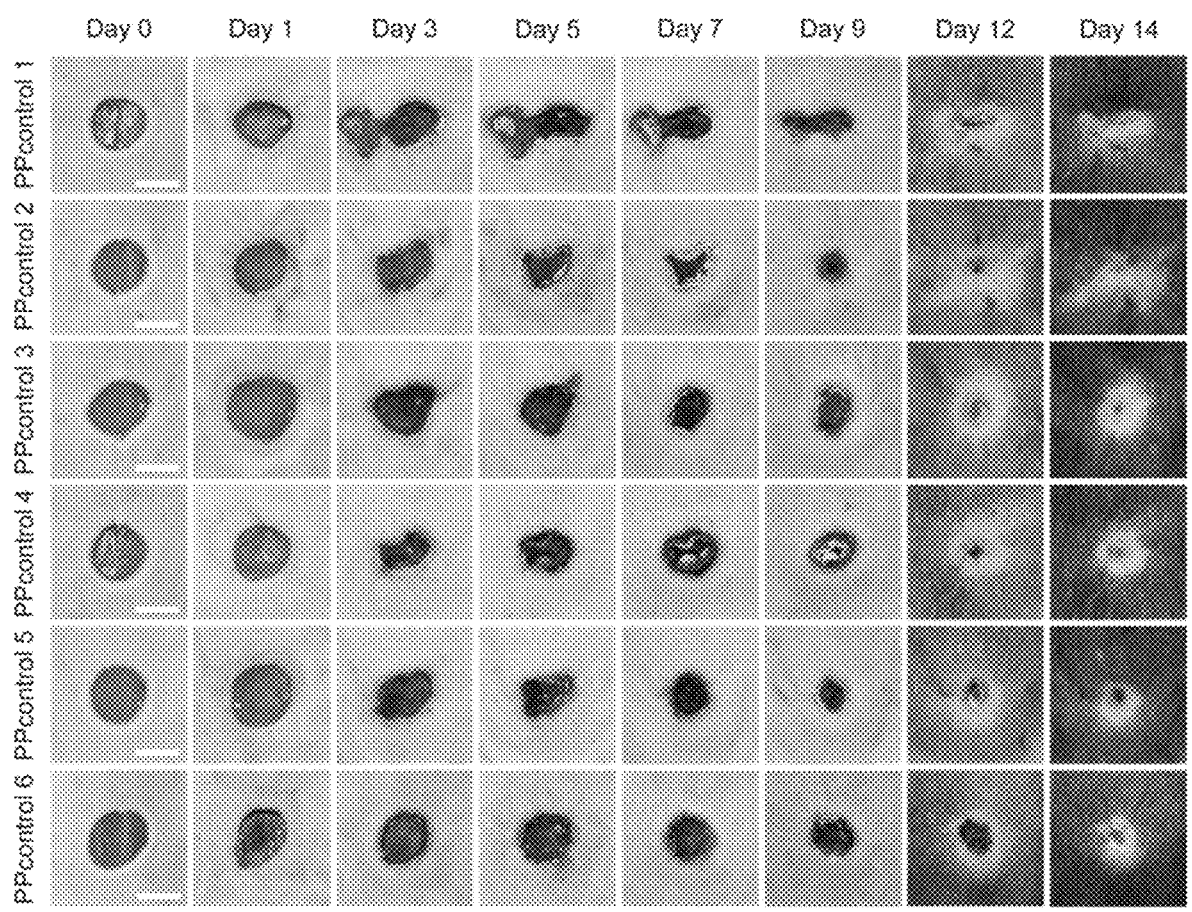
Figure 8D:
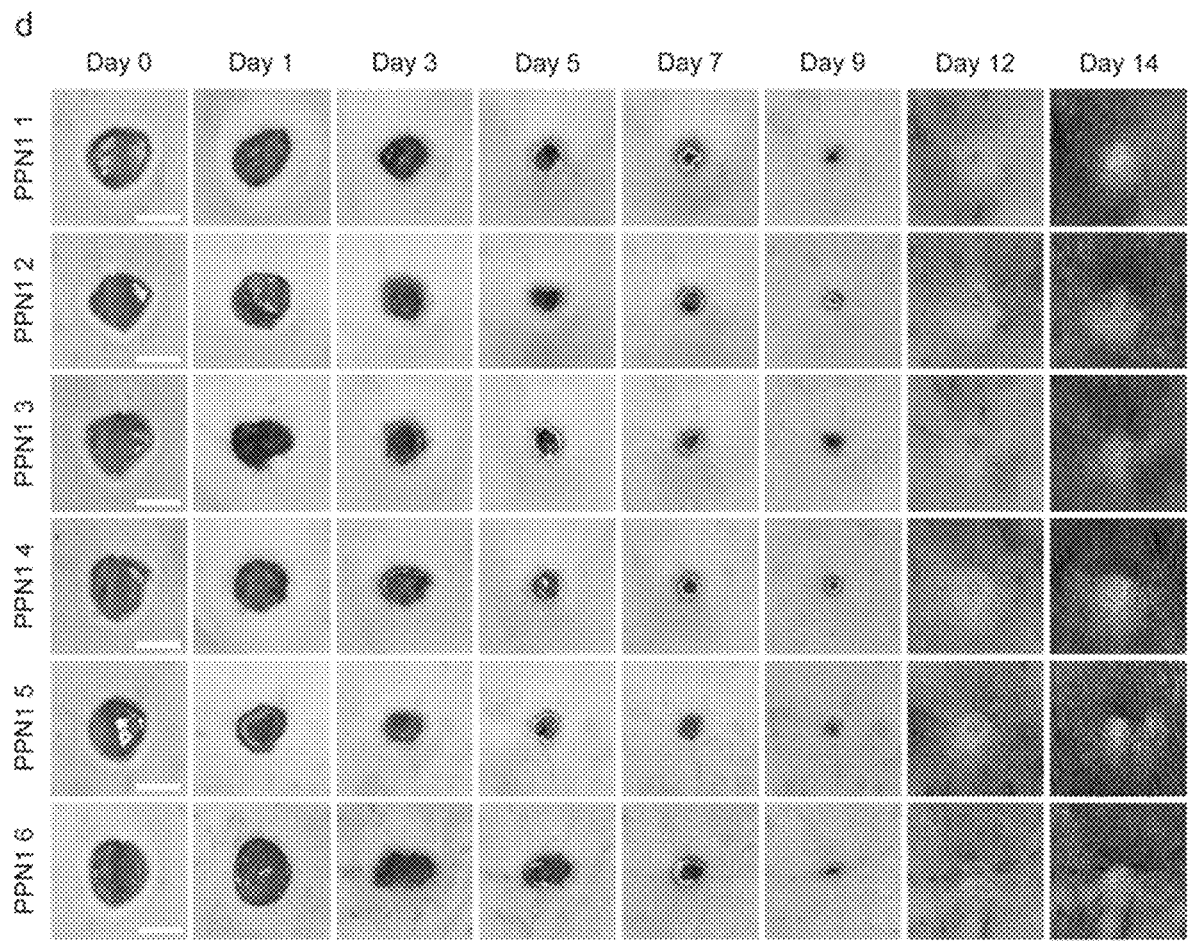

The PPN1 hydrogels were transparent before treatment on infected wound. After 2 days of treatment, the PPN1 hydrogels turned yellowish-brown due to the absorption of wound fluids and dead bacteria. The PPN1 hydrogels were found to remain intact and stable throughout the 2 days of treatment of infected wounds (FIG. 6). Hence, the PPN1 hydrogel is stable under in vivo conditions. The hydrogels were also stable and showed constant mass throughout the incubation with wound fluids (FIG. 7). This proved that PPN1 hydrogel is resistant to degradation by infected wound fluids.

Example 10

To compare healing effect, PPN1 hydrogel (prepared in Example 3), PPcontrol and Allevyn Ag were taken for in vivo wound healing study as described below.

The wounding and infection procedures on mice were the same as described in Example 8. At day 0, mice were wounded and infected with bacteria (MRSA USA300). Untreated wounds were secured with Tegaderm and served as controls, while PPcontrol, PPN1 hydrogel and Allevyn Ag were applied to the wounds and were secured with Tegaderm. Photographs of the wounds were taken before dressing application and on days 1, 3, 5, 7, 9, 12 and 14, and at these points the dressings were replaced with fresh ones. The wound size at each time point was determined using ImageJ software (n=6). A two-tailed Student's t test was used for comparisons. Wound sizes were calculated using the formula (Equation 4):

$$\text{Wound size}(\%) = \frac{\text{wound are on } n^{th} \text{ day}}{\text{wound area on day } 0} \times 100\% \qquad (4)$$

Results and Discussion

We studied the healing of MRSA USA300-infected diabetic wounds treated with PPN1 hydrogel, PPcontrol and Allevyn Ag over a 2-week period (FIG. 5b). The wounds that were treated with PPN1 hydrogel were cleaner and smaller than the untreated control, and PPcontrol and Allevyn Ag treated wounds at all time points (FIG. 5c). The wounds also fully closed at day 12 for the PPN1-treated group but did not close after 2 weeks for the other groups (FIGS. 5b-c). Much more pus was observed on the untreated control wounds over the duration of the study, indicating biofilm formation and high inflammation (FIG. 5c). Furthermore, the untreated control wounds deteriorated and showed erratic healing (FIG. 8). These were most likely caused by the spread of infection from the wound site to the neighbouring skin, and delayed wound healing.

Example 11

To compare the effect of PPN1 hydrogel (prepared in Example 3) and Allevyn Ag on the extent of inflammation in the mice skin, fluorescence-activated cell sorting (FACS) was performed as described below.

Wound infection procedures on mice were the same as described in Example 8, using MRSA USA300 as the test pathogen. The wounds were then treated with PPN1 hydrogel and Allevyn Ag. Untreated infected and uninfected wounds served as controls. Two days post treatment, the wounds including 5 mm of the peripheral region were excised. Single-cell suspensions from wound samples were obtained using gentleMACS Dissociator according to the manufacturer's protocol (Miltenyi Biotec). Cells were immuno-labelled with CD11b and Ly6G (Biolegends) and flow cytometry was carried out using an Accuri C6 flow cytometer (BD Biosciences). Data analysis was performed using Flowjo software version 7.6.5 (Tree Star). The mean percentage values (n=6) were plotted for each treatment, ±SEM. A two-tailed Student's t test was used for comparisons.

Results and Discussion

Figure 9:
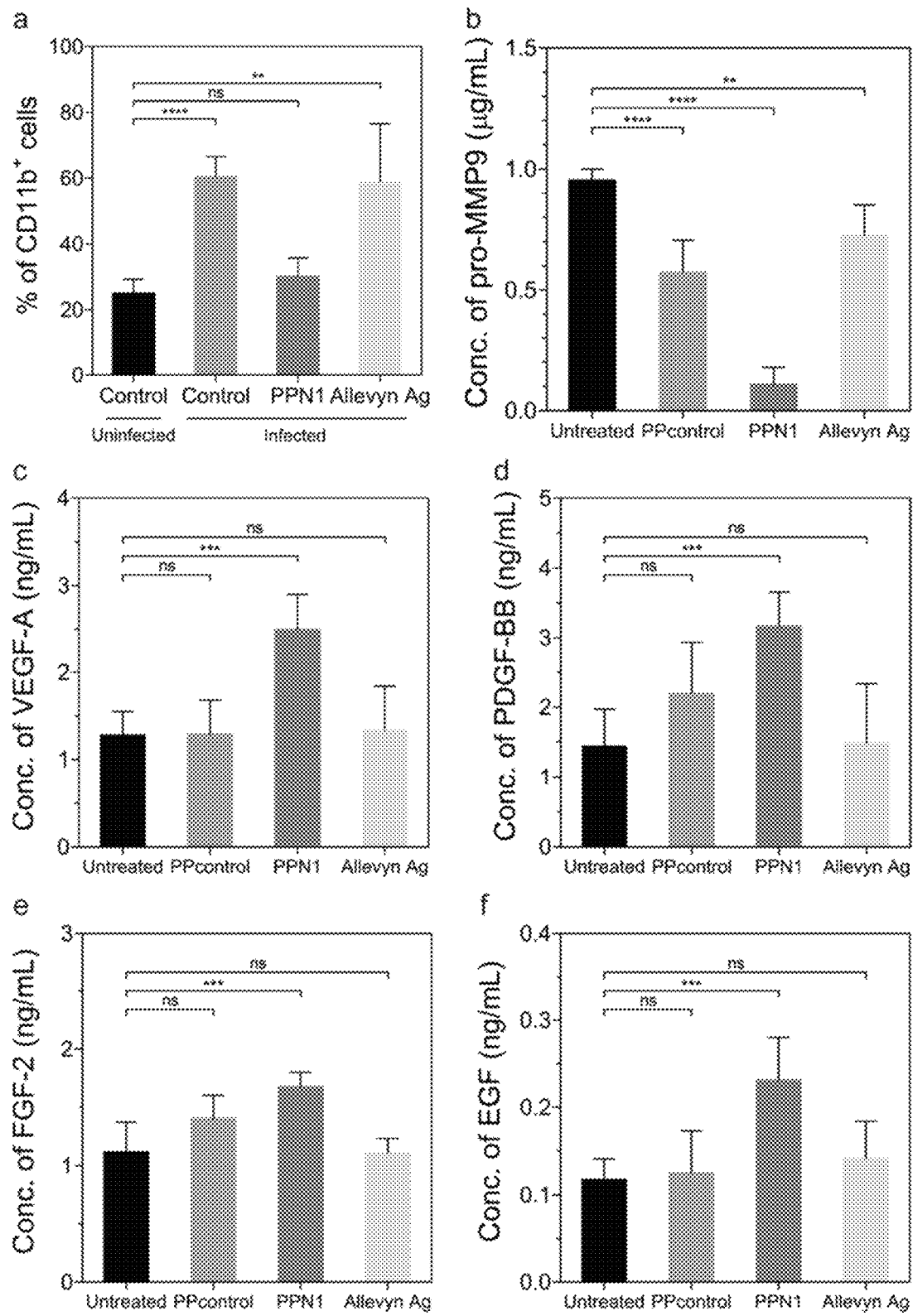
FIG. 9 shows the characterizations of wound tissues. Measurements in MRSA USA300-infected diabetic mice (n=6) made 2 days post-treatment: (a) Percentage of CD11b$^+$ cells in wounds. The percentage of CD11b$^+$ cells is directly proportional to the extent of inflammation in the skin; (b) Concentration of pro-MMP9 in wounds. Concentrations of wound healing factors (c) VEGF-A; (d) PDGF-BB; (e) FGF-2; and (f) EGF in wounds.  denotes P<0.01, * denotes P<0.001 and **** denotes P<0.0001.
Figure 10:
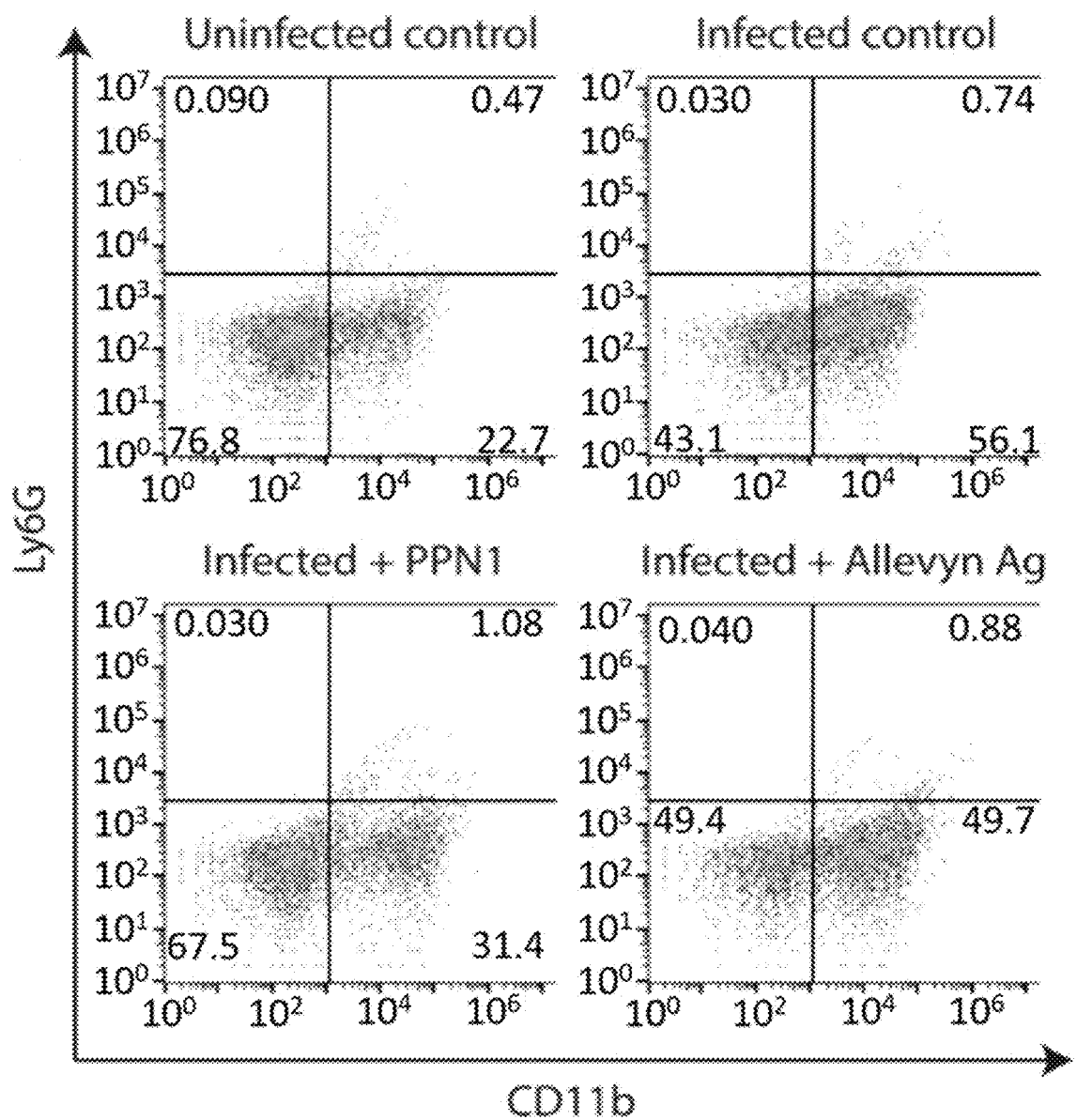
FIG. 10 shows the flow cytometry data of cells taken from wound samples and immuno-labelled with CD11B and Ly6G.

Analysis by FACS showed that the percentage of CD11b$^+$ cells (i.e. leukocytes, which include monocytes, neutrophils, granulocytes and macrophages) increased in untreated infected (by MRSA USA300) wounds (FIG. 9a). However, infected wounds treated with PPN1 hydrogel did not show any excess inflammatory (CD11b$^+$) cells over the levels present in uninfected wounds (FIGS. 9a and 10). The reduction in wound inflammation produced by PPN1 hydrogel is likely due to its killing and removal of bacteria from the wound site. On the other hand, Allevyn Ag did not modulate the number of CD11b$^+$ cells after 2 days of treatment.

Example 12

The wound healing related factors associated with PPN1 hydrogel (prepared in Example 3) were evaluated with ELISA tests described below.

Wound infection procedures were the same as described in Example 8, using MRSA USA300 as the test pathogen. The wounds were then treated with PPcontrol, PPN1 hydrogel and Allevyn Ag. Untreated infected and uninfected wounds served as controls. Two days post treatment, the wounds including 5 mm of the peripheral region were excised. Each wound was homogenized in PBS (900 µL) and centrifuged to remove tissues and bacteria. The supernatants were collected and tested with ELISA kits according to the manufacturer's protocol (pro-MMP9, VEGF-A, PDGF-BB, FGF-2 and EGF, Lonza). The mean concentration values (n=6) were plotted for each treatment, ±SEM. A two-tailed Student's t test was used for comparisons.

Results and Discussion

ELISA tests were used to determine the concentration of wound healing related factors that were present in the wounds at day 3. The concentration of pro-MMP9 (which is a precursor to MMP9 and is detrimental to wound healing (Hariono, M. et al., *Wound Medicine* 2018, 22, 1-13)) was high for the untreated control wounds, whereas PPN1 hydrogel significantly reduced the level of pro-MMP9 in the wounds (FIG. 9b). PPcontrol and Allevyn Ag also significantly reduced pro-MMP9 concentrations (FIG. 9b), though to a lesser degree than PPN1. The concentrations of other wound healing factors (VEGF-A, PDGF-BB, FGF-2 and EFG) were also measured by ELISA and found to be significantly higher in PPN1-treated wounds than in untreated control, and PPcontrol and Allevyn Ag treated wounds (FIGS. 9c-f). Therefore, PIM and NAC in PPN1 that dissociated from the hydrogel network into the wound site suppressed infection in the wound and accelerated wound healing by allowing new blood vessels to form and promoting delivery of wound healing factors as shown by the elevated wound healing factors in the wound tissues.

Comparative Example 1

To investigate the contributions of the individual components (PIM-mal and NAC) towards wound healing, a comparison study was done using in vivo wound healing and ELISA tests as described in Example 10 and 12.

A hydrogel without PIM-mal but containing NAC (denoted as PP-N) and a hydrogel without NAC but containing PIM-mal (denoted PPN-) were prepared as described in Example 3 using the same concentrations of other components as PPN1.

Results and Discussion

Figure 11:
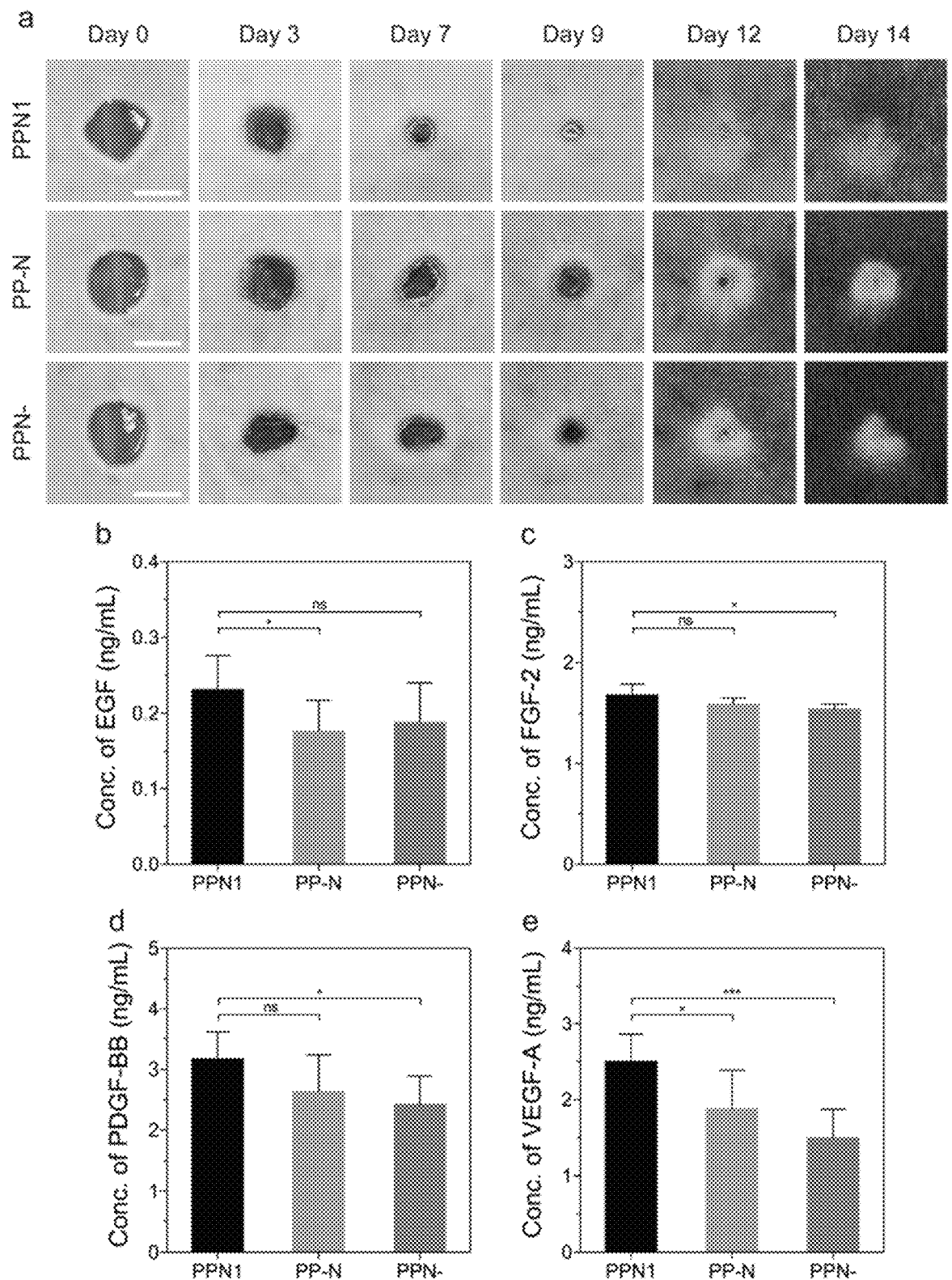
FIG. 11 depicts the (a) Visual appearance of representative PPN1, PP-N and PPN-hydrogel-treated wounds between dressing changes. Scale bar=5 mm; Concentrations of wound healing factors (b) EGF; (c) FGF-2; (d) PDGF-BB; and (e) VEGF-A in wounds. * denotes P<0.05 and *** denotes P<0.001.

PP-N and PPN-treated wounds healed slower than PPN1 treated wounds and they did not completely close after 2 weeks (FIG. 11). The wound healing factors expressed for PP-N and PPN-treated wounds were also, in general, statistically lower than PPN1 treated wounds (FIG. 11). These results proved that PIM and NAC are required to remove biofilm and accelerate wound healing as treatment by the gel controls (without PIM and NAC) did not have significant killing of bacteria and the wounds healed slower. In addition, these results suggest that both the antibacterial PIM-mal and antioxidative NAC work in tandem to accelerate wound healing.

Comparative Example 2

To show the superior antibacterial property of PIM, in vivo wound healing study using cationic polymer polyethylenimine (PEI) as the antibacterial component in hydrogel was carried out as described in Examples 8 and 10 PEI was modified to PEI-mal using the same synthesis strategy as described in Example 1 and formulated into PEI-based hydrogel using the same method as described in Example 3.

Results and Discussion

Figure 12:
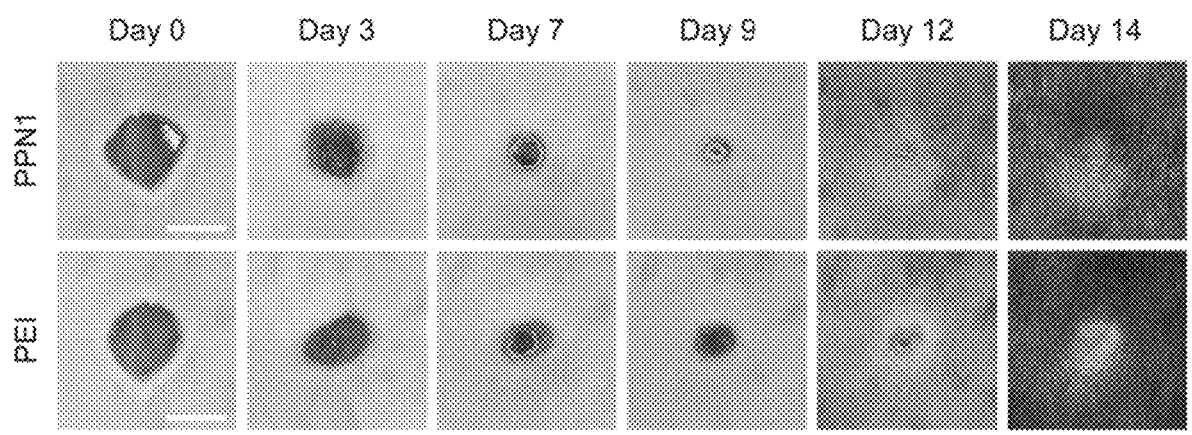
FIG. 12 depicts the visual appearance of representative PPN1- and PEI-based hydrogel-treated wounds between dressing changes. Scale bar=5 mm.

PEI-based hydrogel-treated wounds only fully closed on day 14 while PIM-based hydrogel-treated wounds fully closed on day 12 (FIG. 12). These results show that PIM-based hydrogel encouraged faster healing and treated infected wound better than PEI-based hydrogel.

The invention claimed is:

1. A hydrogel for wound healing comprising:
   a hydrogel polymeric matrix comprising:
      a first polymeric component;
      a second polymeric component, where the first and second polymeric components are crosslinked together to form the hydrogel polymeric matrix; and
      a first portion of a polymeric antimicrobial material capable of crosslinking with the first and/or second polymeric components, said first portion being wholly or partly crosslinked into the hydrogel polymeric matrix;
      a second portion of the polymeric antimicrobial material capable of crosslinking with the first and/or second polymeric components, said second portion being distributed within the hydrogel polymeric matrix but not crosslinked into the hydrogel polymeric matrix;
   wherein the first and second polymeric components are selected from one of the following sets:
      (a) the first polymeric component is derived from a polymeric material comprising at least two thiol functional groups and the second polymeric component is derived from a polymeric material comprising at least two maleimide groups;
      (b) the first polymeric component is derived from a polymeric material comprising at least two thiol functional groups and the second polymeric component is derived from a polymeric material comprising at least two vinyl sulfone groups;
      (c) the first polymeric component is derived from a polymeric material comprising at least two azide functional groups and the second polymeric component is derived from a polymeric material comprising at least two cyclooctynyl groups;
      (d) the first polymeric component is derived from a polymeric material comprising at least two amine functional groups and the second polymeric component is derived from a polymeric material comprising at least two aldehyde groups; and
      (e) the first polymeric component is derived from a polymeric material comprising at least two amine functional groups and the second polymeric component is derived from a polymeric material comprising at least two acrylate groups; and
   optionally, an antioxidant material distributed within the hydrogel polymeric matrix and/or covalently bonded thereto.

2. The hydrogel according to claim 1, wherein the first polymeric component is derived from a polymeric material comprising at least two thiol functional groups and the second polymeric component is derived from a polymeric material comprising at least two maleimide groups.

3. The hydrogel according to claim 2, wherein the first polymeric component is derived from a polymeric material that has from 2 to 8 thiol functional groups and the second polymeric component is derived from a polymeric material that has from 2 to 8 maleimide groups.

4. The hydrogel according to claim 3, wherein the first polymeric component is derived from a multi-arm polyethylene glycol having from 2 to 8 arms that are each terminated by a thiol functional group and the second polymeric component is derived from a multi-arm polyethylene glycol having from 2 to 8 arms that are each terminated by a maleimide group.

5. The hydrogel according to claim 4, wherein the first polymeric component is derived from poly(ethylene glycol)

tetra thiol and the second polymeric component is derived from poly(ethylene glycol) tetra maleimide.

6. The hydrogel according to claim 1, wherein the polymeric antimicrobial material capable of crosslinking with the first and/or second polymeric components is selected from one or more of
   a polycationic polymer terminated by at least two maleimide groups,
   a polycationic polymer terminated by at least one maleimide group and at least one thiol group,
   a polycationic polymer terminated by at least two vinyl sulfone groups,
   a polycationic polymer terminated by at least one vinyl sulfone group and at least one thiol group,
   a polycationic polymer terminated by at least two cyclooctynyl groups,
   a polycationic polymer terminated by at least two azide groups,
   a polycationic polymer terminated by at least one cyclooctynyl group and at least one azide group,
   a polycationic polymer terminated by at least two amino groups,
   a polycationic polymer terminated by at least two aldehyde groups,
   a polycationic polymer terminated by at least one amino group and at least one aldehyde group,
   a polycationic polymer terminated by at least two acrylate groups, and
   a polycationic polymer terminated by at least one amino group and at least one acrylate group provided that said material is capable of forming a crosslink with at least one of the first and second polymeric components.

7. The hydrogel according to claim 1, wherein the polymeric antimicrobial material is a polycationic polymer terminated by at least two maleimide groups.

8. The hydrogel according to claim 7, wherein the polymeric antimicrobial material is a polyimidazolium polymer terminated by two maleimide groups.

9. The hydrogel according to claim 1, wherein the polymeric antimicrobial material capable of crosslinking with the first and/or second polymeric components has a number average molecular weight of from 500 Daltons to 50,000 Daltons.

10. The hydrogel according to claim 9, wherein the polymeric antimicrobial material has a number average molecular weight of from 1,000 Daltons to 15,000 Daltons.

11. The hydrogel according to claim 10, wherein the polymeric antimicrobial material has a number average molecular weight of from 2,000 Daltons to 10,000 Daltons.

12. The hydrogel according to claim 1, wherein the antioxidant material is present and is N-acetyl cysteine.

13. The hydrogel according to claim 1, wherein the hydrogel is in a form selected from a film, nanoparticles and microparticles.

14. A composite material comprising a substrate and a coating formed of a hydrogel as described in claim 1.

15. A kit of parts selected from:
   (i) (ia) a first mixture comprising a first polymer capable of crosslinking with a second polymer and, optionally, an antioxidant material as described in claim 1;
      (ib) a second mixture comprising a second polymer and a polymeric antimicrobial material capable of crosslinking with the first polymer; and
      (ic) a pharmaceutically acceptable solvent;
      or
   (ii) (iia) a first mixture comprising a first polymer capable of crosslinking with a second polymer, and a polymeric antimicrobial material capable of crosslinking with the second polymer, and, optionally, an antioxidant material as described in claim 1;
      (iib) a second mixture comprising a second polymer; and
      (iic) a pharmaceutically acceptable solvent;
      or
   (iii) (iiia) a first mixture comprising a first polymer capable of crosslinking with a second polymer and a polymeric antimicrobial material capable of crosslinking with the second polymer;
      (iiib) a second mixture comprising a second polymer and, optionally, an antioxidant material as described in claim 1; and
      (iiic) a pharmaceutically acceptable solvent;
      or
   (iv) (iva) a first mixture comprising a first polymer capable of crosslinking with a second polymer and, optionally, an antioxidant material as described in claim 1;
      (ivb) a second mixture comprising a second polymer;
      (ivc) a pharmaceutically acceptable solvent; and
      (ivd) a polymeric antimicrobial material capable of crosslinking with the first and second polymers.

16. A method of forming a hydrogel according to claim 1, comprising the steps of:
   (AA) providing at least two separate solutions, each of said solutions containing a solvent, where each of the at least two solutions contain one or more of a first polymer capable of crosslinking with a second polymer, a second polymer capable of crosslinking with the first polymer, a polymeric antimicrobial material capable of crosslinking with the first and/or second polymer, and, optionally, an antioxidant material as described in claim 1, provided that materials that can react together are not contained in the same solution; and
   (BB) mixing the at least two solutions together to form the hydrogel according to claim 1.

17. The kit of parts according to claim 15, wherein one or more of the following apply:
   (A) the first and second polymers are selected from one of the following sets:
      (aa) the first polymer is a polymeric material comprising at least two thiol functional groups and the second polymer is a polymeric material comprising at least two maleimide groups;
      (bb) the first polymer is a polymeric material comprising at least two thiol functional groups and the second polymer is a polymeric material comprising at least two vinyl sulfone groups;
      (cc) the first polymer is a polymeric material comprising at least two azide functional groups and the second polymer is a polymeric material comprising at least two cyclooctynyl groups;
      (dd) the first polymer is a polymeric material comprising at least two amine functional groups and the second polymer is a polymeric material comprising at least two aldehyde groups; and
      (ee) the first polymer is a polymeric material comprising at least two amine functional groups and the second polymer is a polymeric material comprising at least two acrylate groups;
   (B) the first polymer is a polymeric material that has from 2 to 8 thiol functional groups and the second polymer is a polymeric material that has from 2 to 8 maleimide groups;

(C) the polymeric antimicrobial material capable of crosslinking with the first and/or second polymers is selected from one or more of a polycationic polymer terminated by at least two maleimide groups, a polycationic polymer terminated by at least one maleimide group and at least one thiol group, a polycationic polymer terminated by at least two vinyl sulfone groups, a polycationic polymer terminated by at least one vinyl sulfone group and at least one thiol group, a polycationic polymer terminated by at least two cyclooctynyl groups, a polycationic polymer terminated by at least two azide groups, a polycationic polymer terminated by at least one cyclooctynyl group and at least one azide group, a polycationic polymer terminated by at least two amino groups, a polycationic polymer terminated by at least two aldehyde groups, a polycationic polymer terminated by at least one amino group and at least one aldehyde group, a polycationic polymer terminated by at least two acrylate groups, and a polycationic polymer terminated by at least one amino group and at least one acrylate group provided that said material is capable of forming a crosslink with at least one of the first and second polymers; and (D) the polymeric antimicrobial material capable of crosslinking with the first and/or second polymers has a number average molecular weight of from 500 Daltons to 50,000 Daltons.

18. A method of wound healing comprising applying a hydrogel according to claim 1 to a subject in need thereof.

19. The method according to claim 18, wherein the hydrogel is formed in situ at a wound site on the subject.

* * * * *